US012667508B2

(12) United States Patent
Patmore et al.

(10) Patent No.: US 12,667,508 B2
(45) Date of Patent: Jun. 30, 2026

(54) SHIELD ASSEMBLIES FOR USE WITH PATIENT SUPPORT APPARATUSES

(71) Applicant: Stryker Corporation, Kalamazoo, MI (US)

(72) Inventors: Kevin M. Patmore, Plainwell, MI (US); Arthur Carlos Pallar Da Silva, Saint Joseph, MI (US); Carolyn Fahey, Middleborough, MA (US); Brandon Joseph Morse, Vicksburg, MI (US); Joshua Buck, Grand Rapids, MI (US); Aaron Douglas Furman, Kalamazoo, MI (US); Steven Michael Murphy, Portage, MI (US); Ryan Thomas Slusarzyk, Byron Center, MI (US); Mackenzie Van Loon, Mattawan, MI (US)

(73) Assignee: Stryker Corporation, Portage, MI (US)

( * ) Notice: Subject to any disclaimer, the term of this patent is extended or adjusted under 35 U.S.C. 154(b) by 911 days.

(21) Appl. No.: 17/918,743

(22) PCT Filed: Apr. 15, 2021

(86) PCT No.: PCT/US2021/027386
§ 371 (c)(1),
(2) Date: Oct. 13, 2022

(87) PCT Pub. No.: WO2021/211781
PCT Pub. Date: Oct. 21, 2021

(65) Prior Publication Data
US 2023/0233393 A1 Jul. 27, 2023

Related U.S. Application Data

(60) Provisional application No. 63/052,559, filed on Jul. 16, 2020, provisional application No. 63/017,844, (Continued)

(51) Int. Cl.
| | | |
|---|---|---|
| *A61G 10/00* | (2006.01) | |
| *A61B 46/20* | (2016.01) | |
| *A61B 90/00* | (2016.01) | |

(52) U.S. Cl.
CPC ............ *A61G 10/005* (2013.01); *A61B 46/20* (2016.02); *A61B 90/05* (2016.02)

(58) Field of Classification Search
CPC .......... A61G 10/005; A61B 4/20; A61B 4/40; A61B 2046/205; A61B 46/20; E04H 15/44; E04H 15/46; E04H 15/48; E04H 15/54
See application file for complete search history.

(56) References Cited

U.S. PATENT DOCUMENTS

| | | | |
|---|---|---|---|
| 2,209,801 A | 7/1940 | Valverde | |
| 6,500,111 B1 * | 12/2002 | Salmon | .................. A61G 11/00 600/22 |

(Continued)

FOREIGN PATENT DOCUMENTS

WO 2022182394 A1 9/2022

OTHER PUBLICATIONS

Amazon, "Allen Sports JTX-1 Trailer/Swivel Wheel Jogger Webpage" https://www.amazon.com/Allen-Sports-Trailer-Swivel-Jogger/dp/B00NJZDHXA/ref=sr_1_1?dchild=1&keywords=allen%2Bsports%2Bjtx-1%2Btrailer%2Fswivel%2Bwheel%2Bjogger&qid=1586466710&sr=8-1&th=1&language=en_US, 2020, 7 pages.

(Continued)

*Primary Examiner* — Carrie R Dorna
(74) *Attorney, Agent, or Firm* — Howard & Howard Attorneys PLLC

(57) ABSTRACT
A shield assembly for providing a barrier adjacent to a patient disposed on a patient support apparatus. The shield assembly comprises a support frame defining a closed (Continued)

periphery and including a resilient element extending along the closed periphery to resiliently urge the support frame toward a bias frame shape. A barrier panel is coupled to the support frame and spans the closed periphery. The shield assembly may further include a base operatively attached to the support frame to selectively place the support frame in a contour frame shape. Tension in the resilient element effected by the base holding the support frame in the contour frame shape places the barrier panel in a curved configuration to define a patient accommodation space shaped to receive the patient adjacent to the base and to the barrier panel.

19 Claims, 24 Drawing Sheets

Related U.S. Application Data filed on Apr. 30, 2020, provisional application No. 63/010,535, filed on Apr. 15, 2020.

(56) References Cited

U.S. PATENT DOCUMENTS

| | | | | |
|---|---|---|---|---|
| 7,398,571 | B2 | 7/2008 | Souke et al. | |
| 9,644,390 | B1 * | 5/2017 | Garvens | A47C 21/00 |
| 2012/0284916 | A1 | 11/2012 | Hill | |
| 2013/0276847 | A1 * | 10/2013 | Vulich | E04H 15/405 |
| | | | | 135/124 |
| 2016/0115704 | A1 | 4/2016 | Burke | |

OTHER PUBLICATIONS

Burchett, Caitlyn, "Portable Patient Pod Protects EMS Crews", Perry News-Herald Taco Times, 2020, 2 pages.
Coolman, Robert, "E-Skin That Changes Color Like a Chameleon", Daily Beast, https://www.thedailybeast.com/e-skin-that-changes-color-like-a-chameleon?ref=scroll, Sep. 15, 2015, 19 pages.
Ferno, "Patient Shield Website", 2020, 3 pages.
International Search Report for Application No. PCT/US2021/027386 dated Jul. 16, 2021, 1 page.
Liverpool University Hospitals NHS Foundation Trust, ""Aintree Doctor Sees Idea of Pop-Up Dome to Shield Staff from COVID-19 Turned Into Reality in Just Eight Days"", https://www.liverpoolft.nhs.uk/news/aintree-doctor-sees-idea-of-a-pop-up-dome-to-shield-staff-from-covid-19-turned-into-reality-in-just-eight-days/?fbclid=IwARDJWdVJVwqhO-_JIYNF19mdAYy18Kjr7TreDYrfx4ulNU3PqKb15WzMtvs, May 6, 2020, 3 pages.
PR Web, "Events Company T3 Expo Creates Double Hoop Bed Tents for Local Massachusetts Hospitals to Help Healthcare Workers Better Service Intubated Covid-19 Patients", May 7, 2020, 4 pages.
Quigg, Charlie, "Plastics Change Color—and Back—In Less Than 1 Second", Scientific American, Chemistry World, https://www.scientificamerican.com/article/plastics-change-color-and-back-in-less-than-1-second/, Jul. 25, 2014, , 3 pages.
Willis, Preston, ""LinkedIn Post—I Love the Innovation Our Customers Have-Covid Cover", https://www.linkedin.com/feed/update/urn:li:activity:6649024440594165760/, 2020, 1 page."

* cited by examiner

SHIELD ASSEMBLIES FOR USE WITH PATIENT SUPPORT APPARATUSES

CROSS-REFERENCE TO RELATED APPLICATIONS

The subject patent application claims priority to and all the benefits of U.S. Provisional Patent Application No. 63/010,535, filed on 15 Apr. 2020, U.S. Provisional Patent Application No. 63/017,844, filed on 30 Apr. 2020, and U.S. Provisional Patent Application No. 63/052,559, filed on 16 Jul. 2020, the entire contents and disclosure of each of which are hereby incorporated by reference in their entirety.

BACKGROUND

Patient support apparatuses, such as hospital beds, stretchers, cots, tables, wheelchairs, chairs, and the like, are used to help caregivers facilitate care of patients in a health care setting. In certain medical situations, such as those involving treatment and/or transport of patients with communicable diseases, caregivers frequently utilize various types of personal protective equipment such as gloves, masks, and the like, when interacting with patients.

In addition to personal protective equipment worn or otherwise utilized by caregivers, various types of barriers may be employed to afford patients with additional protection from communicable disease, such as for example isolettes used in the care of newborn infants and similar barriers utilized in the care of patients with compromised immune systems. In addition to affording protection to the patient from exposure to communicable diseases, it will be appreciated that these types of barriers can also help limit the spread of communicable diseases from infected patients to other patients, bystanders, caregivers, and the like.

Those having ordinary skill in the art will appreciate that conventional patient barriers may be relatively large in size, tend to be expensive to manufacture, and can be difficult to utilize in emergency situations that necessitate patient transport quickly from one place to another. For example, an injured patient with a compromised immune system may be at significantly increased risk of exposure to communicable disease when being transported from their home to a health care facility. Similarly, a patient infected with a relatively contagious communicable disease may pose a significant risk of exposure to caregivers, bystanders, and the like when being transported from their home to a health care facility.

While patient-centric barriers are known, those having ordinary skill in the art will appreciate that they tend to be bulky and difficult to store when not needed, are time consuming to deploy when needed, can be difficult to clean or otherwise sanitize between uses, and may be relatively expensive such that they are reserved for specific transport situations.

While conventional types of personal protective equipment, patient barriers, and the like have generally worked well for their intended purposes, there remains a need in the art for overcoming one or more of the disadvantages noted above.

SUMMARY

The present disclosure provides a shield assembly for providing a barrier adjacent to a patient disposed on a patient support apparatus. The shield assembly includes a support frame defining a closed periphery. The support frame has a resilient element extending along the closed periphery to resiliently urge the support frame toward a bias frame shape. A barrier panel is coupled to the support frame and spans the closed periphery. A base is operatively attached to the support frame to selectively place the support frame in a contour frame shape, different from the bias frame shape, and to limit resilient movement of the support frame toward the bias frame shape. Tension in the resilient element effected by the base holding the support frame in the contour frame shape places the barrier panel in a curved configuration to define a patient accommodation space shaped to receive the patient adjacent to the base and to the barrier panel.

The present disclosure also provides a shield assembly for providing a barrier adjacent to a patient disposed on a patient support apparatus. The shield assembly includes a support frame defining a closed periphery. The support frame has a resilient element extending along the closed periphery to resiliently urge the support frame toward a bias frame shape. A barrier panel is coupled to the support frame and spans the closed periphery. A drape panel is coupled to the support frame and extends away from the closed periphery to a drape edge. A base is operatively attached to the support frame to selectively place the support frame in a contour frame shape, different from the bias frame shape, and to limit resilient movement of the support frame toward the bias frame shape. Tension in the resilient element effected by the base holding the support frame in the contour frame shape places the barrier panel in a curved configuration to define a patient accommodation space shaped to receive the patient adjacent to the base and to the barrier panel. The drape panel defines a draped area in communication with the patient accommodation space when the support frame is disposed in the contour frame shape.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION OF THE EMBODIMENTS

Figure 1:
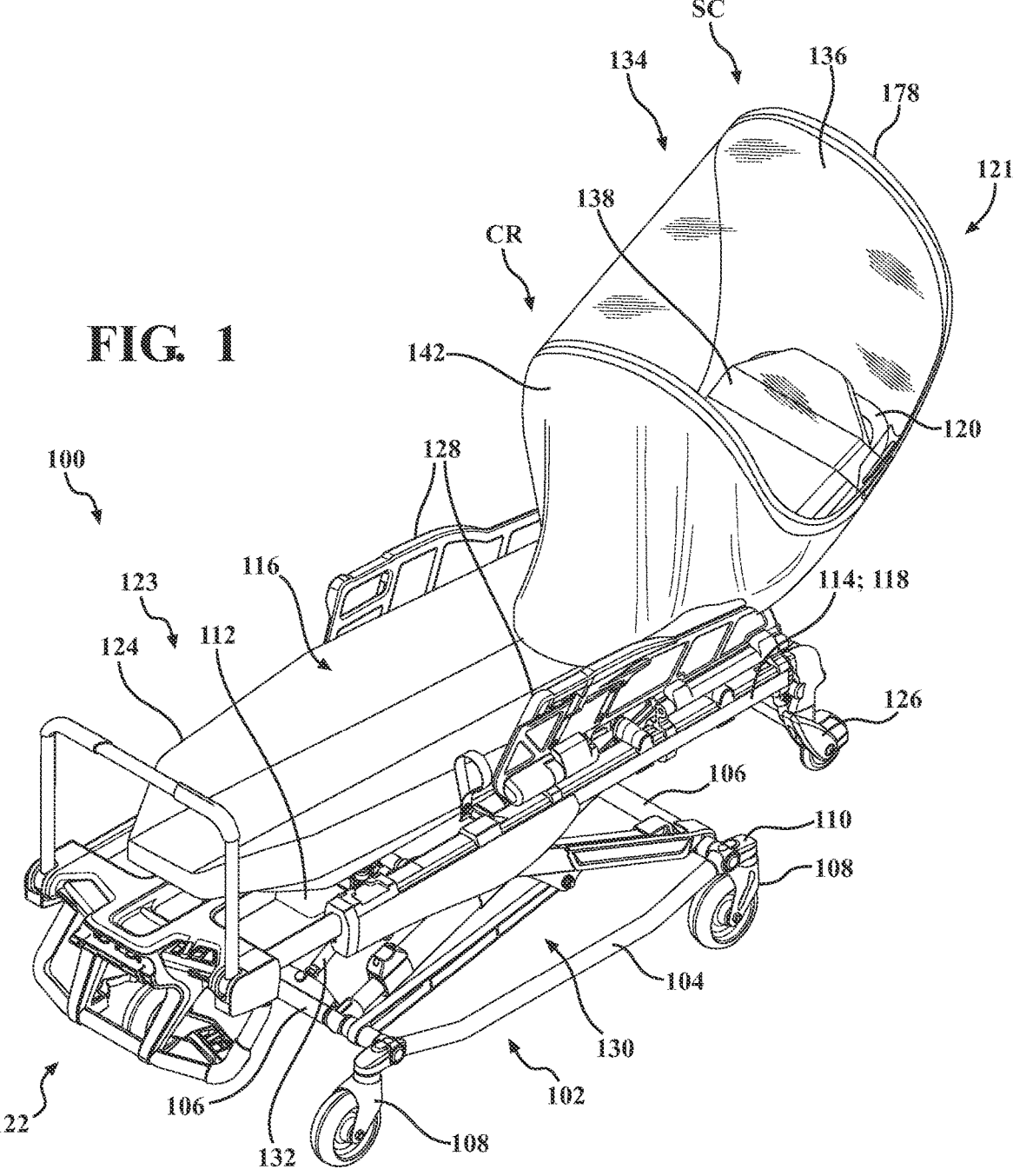
FIG. 1 is a perspective view of a patient support apparatus shown having a litter with a back section to which a shield assembly is secured, according to embodiments of the present disclosure.
Figure 2:
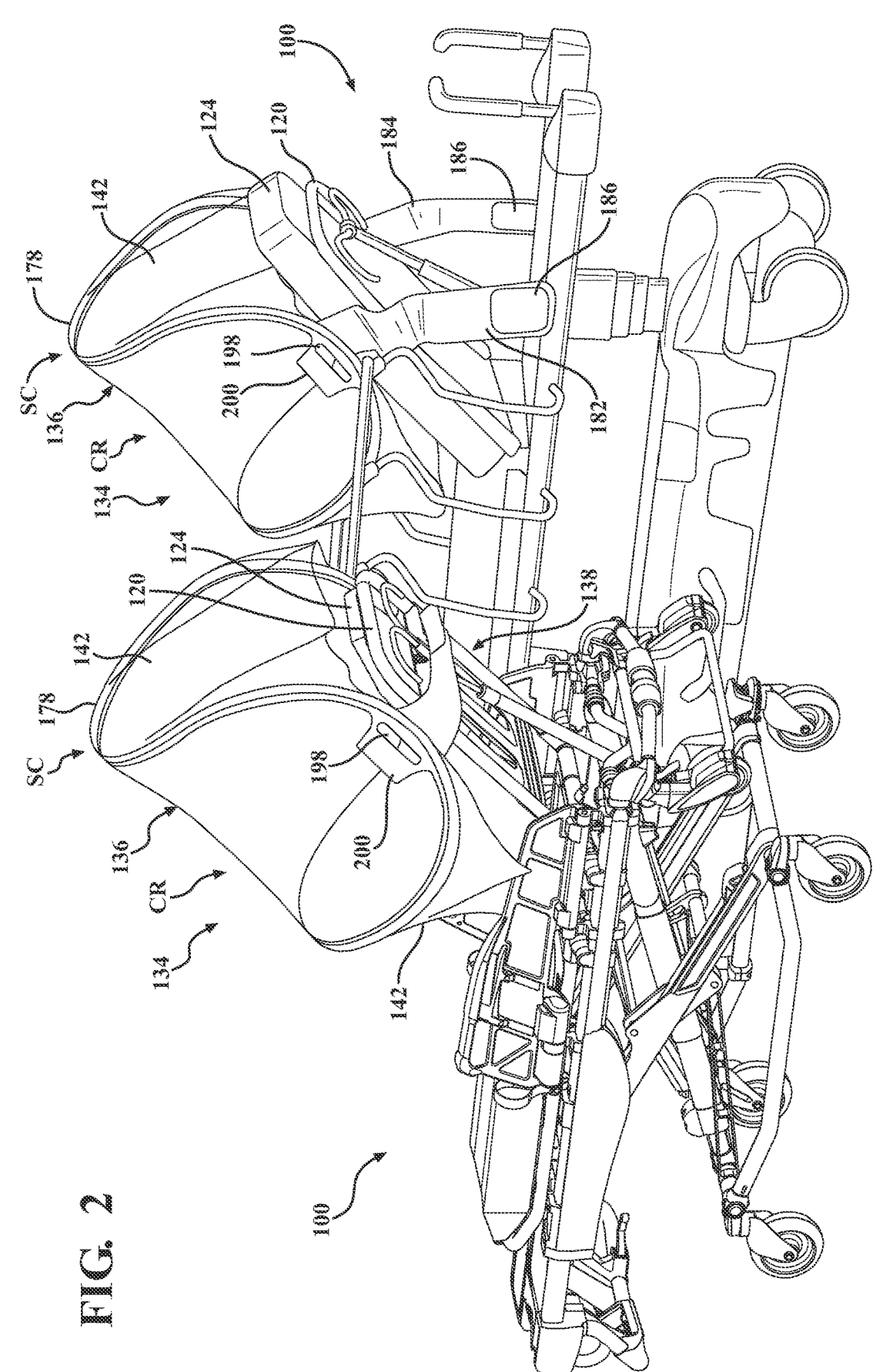
FIG. 2 is a perspective view of the patient support apparatus and shield assembly of FIG. 1, shown positioned adjacent to another type of patient support apparatus, defined as a patient support apparatus, having a respective back section onto which another shield assembly is positioned.
Figure 3:
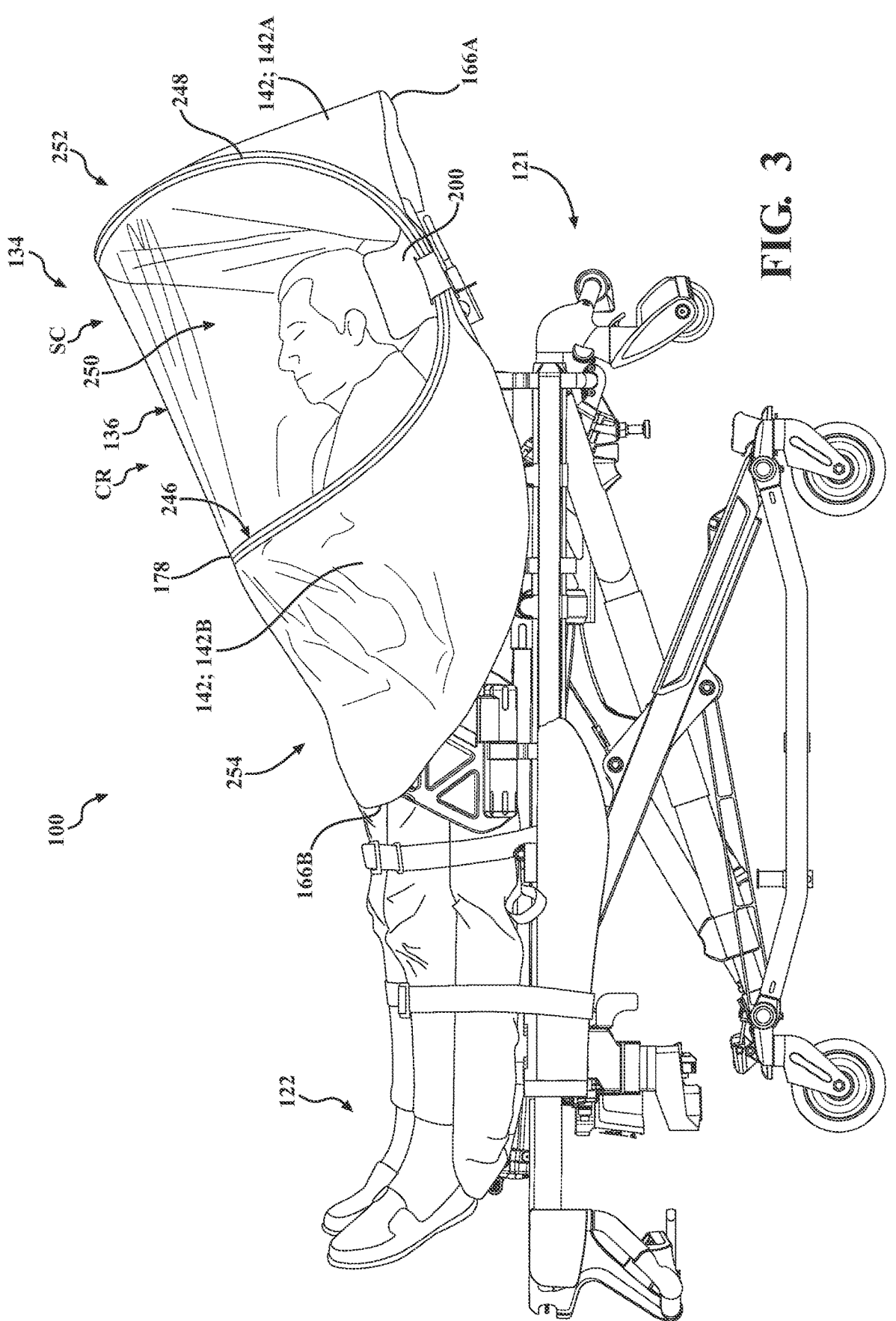
FIG. 3 is a perspective view of a patient support apparatus shown having a litter supporting a patient, the litter having a back section to which a shield assembly is secured, according to embodiments of the present disclosure.

Referring to FIGS. 1-3, a patient support apparatus 100 is shown for supporting a patient in a health care and/or transportation setting. The patient support apparatus 100 illustrated in FIG. 1 is realized as a cot. However, it will be appreciated that other types of patient support apparatuses 100 are contemplated by the present disclosures, such as for example stretchers, beds, tables, wheelchairs, chairs, and/or similar apparatuses utilized in the transportation and/or care of a patient.

The patient support apparatus 100 illustrated in FIG. 1 generally comprises a support structure to provide support for the patient. The support structure comprises a base frame 102 with longitudinally extending side rails 104 and laterally extending rails 106 interconnected at the ends thereof to the side rails 104 to form a rectangle. A plurality of caster wheel assemblies 108 are operatively connected proximate each corner of the rectangular shaped base frame 102 formed by the side rails 104 and the rails 106. The wheel assemblies 108 may be configured to swivel to facilitate turning of the patient support apparatus 100. One or more of the wheel assemblies 108 may comprise a swivel locking mechanism to prevent the wheel assembly 108 from swiveling when engaged. The caster wheel assemblies 108 may also comprise a wheel brake 110 to prevent rotation of the wheel. It will be appreciated that various types of support structures, including with different types and configurations of base frames 102, are contemplated by the present disclosure.

The support structure further comprises a litter 112 comprising a litter frame 114. The litter 112 includes or otherwise defines a patient support deck having a patient support surface 116 configured to support a patient. In the representative embodiment illustrated herein, the litter frame 114 includes side rails 118 that extend longitudinally adjacent to the patient support surface 116. The patient support surface 116 may be comprised of one or more articulable sections, for example, a back section 120 arranged adjacent to a patient's back at a first longitudinal end 121 of the patient support apparatus 100, a foot section 123 arranged adjacent to a patient's feet at a second longitudinal end 122 of the patient support apparatus, and other sections between the back section 120 and the foot section 123, such as a seat section, a leg section, and the like (not shown in detail). The back section 120 and the foot section 123 facilitate care and/or transportation of the patient. One or more mattresses 124 may be supported on the litter 112 to provide support for the patient, and could likewise define the patient support surface 116.

The litter 112 includes loading wheels 126 extending from the litter frame 114 proximate the back section 120 to facilitate loading and unloading of the patient support apparatus 100 from a vehicle. For example, the loading wheels 126 may be positioned and configured to facilitate loading and unloading the patient support apparatus 100 into an ambulance. Hand rails 128 extend from opposing sides of the litter frame 114 to provide egress barriers for the patient when situated on the patient support surface 116. The hand rails 128 may also be utilized by an individual, such as a caregiver, an emergency medical technician (EMT), or other medical professional, to move or manipulate the patient support apparatus 100. The hand rails 128 may comprise a hinge, pivot, or similar mechanism to allow the hand rails 128 to be folded or stored at or below the plane of the patient support surface 116.

A lift mechanism 130 is provided between the base frame 102 and the litter 112 to facilitate raising and lowering of the litter 112 relative to a transport surface (e.g., a floor surface). The lift mechanism 130 is configured to facilitate adjusting the height of the litter 112 to a maximum height, a minimum height, or any intermediate height in between the maximum and minimum heights. The lift mechanism 130 may comprise a powered actuator system which employs one or more actuators 132, as illustrated in FIGS. 1-3, configured to raise and lower the litter 112. The lift mechanism 130 may be similar to as is described in U.S. Pat. No. 7,398,571, filed on Jun. 30, 2005, entitled, "Ambulance Cot and Hydraulic Elevating Mechanism Therefor," the disclosure of which is hereby incorporated by reference. Other configurations are contemplated.

Referring to FIGS. 1-24, shield assemblies 134 are generally shown in various configurations according to embodiments of the present disclosure. As will be appreciated from the subsequent description below, the shield assemblies 134 facilitate providing a barrier between caregivers and a patient supported on the litter 112 of the patient support apparatus 100, as well as during movement of the patient between different patient support apparatuses 100 and/or patient transport apparatuses. To this end, the shield assemblies 134 each generally include a barrier panel 136 which defines the barrier, and a base 138 operatively attached to the barrier panel 136. The base 138 facilitates, among other things, securing, placing, locating, or otherwise supporting the shield assembly 134 to the back section 120 (or another portion of the litter 112) of the patient support apparatus 100. The various components of the shield assemblies 134 introduced above will each be described in greater detail below.

As noted above, the shield assemblies 134 of the present disclosure employ the barrier panel 136 to facilitate providing the barrier adjacent to the patient. In some embodiments, the barrier panel 136 may be formed from a thin, flexible material (e.g., a film, fabric, and the like), such as is described in greater detail below in connection with FIGS. 1-22. In some embodiments, the barrier panel 136 may be formed from a semi-rigid, flexible material (e.g., plastic sheet/panels), such as is described in greater detail below in connection with FIGS. 23-24. While various materials are contemplated by the present disclosure, in some embodiments, the barrier panel 136 may be formed from one or more of thermoplastic polyurethane, polyethylene, polyvinyl chloride, and/or fabrics, woven materials, and the like, which may be treated, coated, and/or otherwise configured to inhibit the transmission of particulates, contaminants, moisture, and the like (e.g., liquid impermeable), and/or combinations of different materials. In some embodiments, the barrier panel 136 may comprise one or more air permeable (e.g., "breathable") materials that allow air, but not moisture, to be exchanged across the barrier (e.g., similar to as is used in an N95 mask). In some embodiments, the barrier panel 136 and/or other portions of the shield assembly 134 may be formed from multiple materials, some of which may be substantially transparent (e.g., "clear"), semi-transparent (e.g., "frosted" and/or "tinted"), and/or non-transparent (e.g., opaque), as is described in greater detail below. Beyond providing the barrier between the patient and caregiver, it will be appreciated that the shield assemblies 134 of the present disclosure may also be utilized to provide the patient with protection from the outside environment (e.g., a rain barrier, a sunshade, and the like). In some embodiments, the barrier panel 136 and/or other portions of the shield assembly 134 may be provided with patterns, colors, symbols, indicia, and the like (not shown in detail) to, among other things, promote improved patient comfort.

In some embodiments, one or more components of the shield assemblies 134 may be realized as disposable (e.g., "single-use") components, or may be re-usable, cleanable, sterilizable, and the like. In some embodiments, the shield assemblies 134 may be stored in a sterile, sealed container or packaging (not shown). Those having ordinary skill in the art will appreciate that components and/or structural features of the various shield assemblies 134 depicted throughout the drawings can be combined or otherwise implemented in other embodiments of the present disclosure. Thus, various configurations are contemplated by the present disclosure other than the discrete embodiments illustrated throughout the drawings.

Referring now to FIGS. 1-6, an embodiment of a shield assembly 134 according to the present disclosure is shown. In this embodiment, both the barrier panel 136 and the base 138 are operatively attached to a support frame 178. The support frame 178 defines a closed periphery 246 and includes a resilient element 248 extending along the closed periphery 246 to resiliently urge the support frame 178 towards a bias frame shape SB (see FIG. 7), as described in greater detail below. The barrier panel 136 is coupled to the support frame 178 and spans the closed periphery 246. The base 138 is operatively attached to the support frame 178 to selectively place the support frame 178 in a contour frame shape SC (see FIG. 4), different from the bias frame shape SB, and to limit resilient movement of the support frame 178 towards the bias frame shape SB. Here, tension in the resilient element 248 effected by the base 138 holding the support frame 178 in the contour frame shape SC places the barrier panel 136 in a curved configuration CR to define a patient accommodation space 250 shaped to receive the patient adjacent to the base 138 and to the barrier panel 136. Each of the components of the shield assembly 134 introduced above will be described in greater detail below.

The resilient element 248 may be manufactured from metal, plastic, composites (e.g., fiber rods, tubes, and the like), or other suitable materials, and is generally resiliently flexible (e.g., capable of a certain amount of deflection without permanently deforming or breaking). In some embodiments, the resilient element 248 could be manufactured from a single piece of material (e.g., a rod, tube, and the like manufactured from fiber glass, carbon fiber, spring steel, or another suitable material) that is attached at its respective ends using adhesives, welding, bonding, crimping, or other suitable methods of facilitating mechanical attachment. To this end, in some embodiments, a crimp 179

(see FIG. 6; not shown in detail) manufactured from metal, plastic, or another suitable material could be used to mechanically couple the ends of the resilient element 248. It will be appreciated that the crimp 179 may be releasably attachable, or could be configured to generally retain the ends of the resilient element 248 to form the closed periphery 246 as shown throughout the various embodiments illustrated in the drawings. Other configurations are contemplated.

Figure 7:
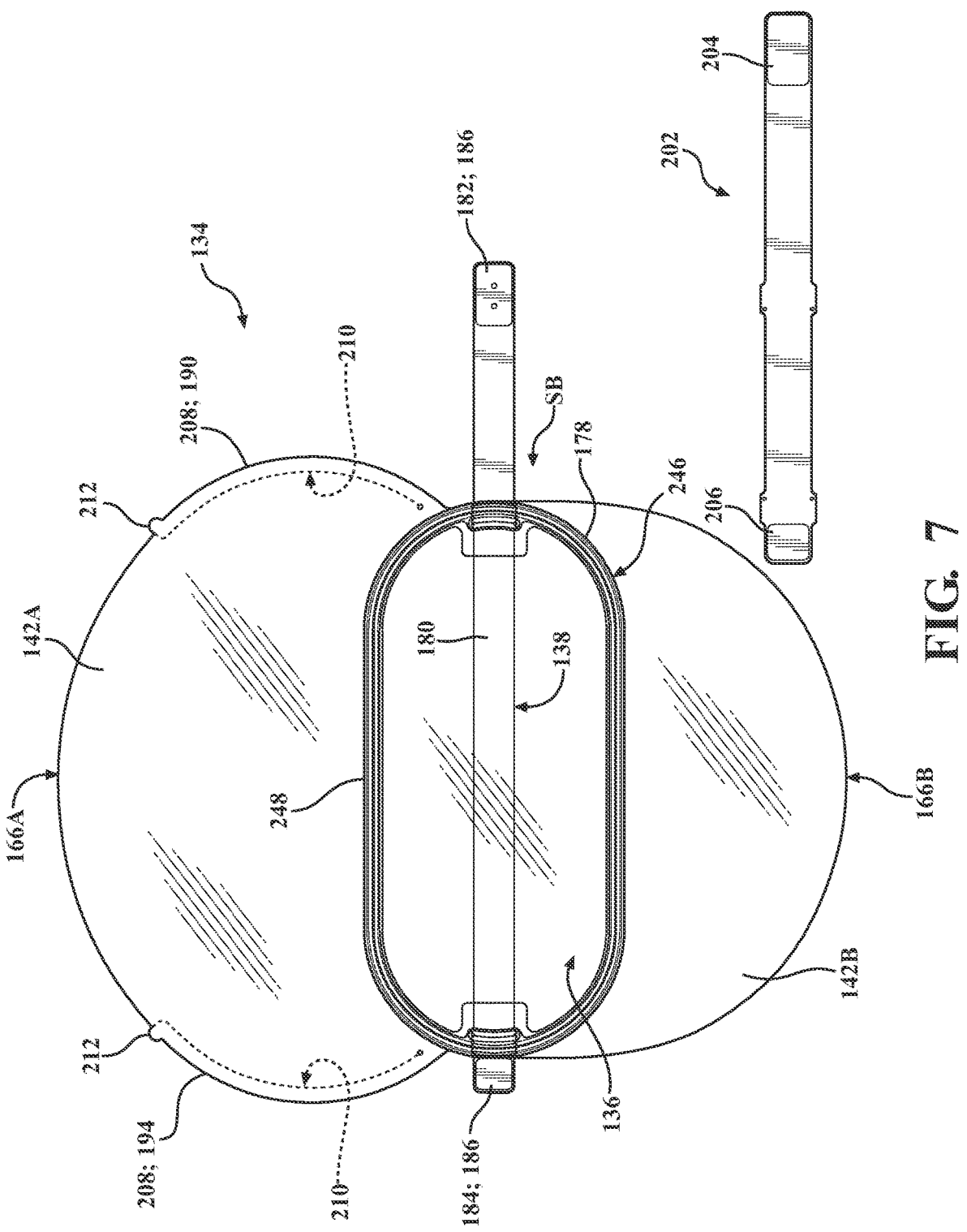
FIG. 7 is a top-side plan view of a shield assembly arranged adjacent to an extension strap according to embodiments of the present disclosure, the shield assembly shown including first and second drapes and a barrier panel operatively attached to a support frame coupled to a base, the support frame is shown in a bias frame shape and the first drape is shown having perforated paths for defining drape straps for securing the shield assembly to a patient support apparatus.

As noted above, the resilient element 248 extends along the closed periphery 246 and resiliently urges the support frame 178 towards the bias frame shape SB (see, for example, FIG. 7). As used herein, the term "bias frame shape SB" refers to the shape and/or profile that the support frame 178 and/or the resilient element 248 adopts in the absence of external forces (e.g., without the base 138 attached). In the representative embodiment illustrated herein, the bias frame shape SB has an elongated, rounded profile (e.g., a "stadium" shape). However, it will be appreciated that other shapes, profiles, and the like are contemplated. In some embodiments, the bias frame shape SB may be defined at least partially based on how the resilient element 248 is formed, and/or how the resilient element 248 is retained, such as via attachment to the barrier panel 136 (e.g., held in, or substantially limited from moving out of, the stadium shape via the barrier panel 136). Here, for example, the representative embodiment of the resilient element 248 illustrated herein is realized as an elongated rod having respective ends joined via the crimp 179 could tend to form a generally circular shape, but attachment to the barrier panel 136 prevents the resilient element 248 from achieving a circular shape and places the resilient element 248 in the stadium-shaped profile of the bias frame shape SB as illustrated in FIG. 7. Here, tension in the resilient element 248 exerts force that urges the closed periphery CP, and therefore the support frame 178, toward the bias frame shape SB. It will be appreciated that when the support frame 178 is in the bias frame shape SB, both the barrier panel 136 and the resilient element have a substantially "flat" profile (see FIG. 7).

In some embodiments, the closed periphery 246 of the support frame 178 may have an elongated, generally rounded-rectangular profile (e.g., a "stadium" shape as noted above) to which one or more pieces of fabric, cloth, or other relatively flexible materials are operatively coupled to define or otherwise form the barrier panel 136 and/or one or more drape panels 142, as described in greater detail below. In some embodiments, such as where thermoplastic polyurethane is utilized for the barrier panel 136 or other portions of the shield assembly 134, pieces of material could be welded or otherwise bonded together and/or to themselves around and/or to the support frame 178 (e.g., around or otherwise to the resilient element 248). It is also contemplated that the barrier panel 136 could be removed and replaced from the support frame 178 in some embodiments. Other configurations are contemplated.

As noted above, the shield assembly 134 employs the base 138 to, among other things, facilitate selectively placing (and holding) the support frame 178 in the contour frame shape SC which, in turn, places the barrier panel 136 in the curved configuration CR to define the accommodation space 250 for the patient. To this end, in some embodiments, the base 138 may include or otherwise be realized as a strap 180 (see, for example, FIGS. 2, 4, 7-8, 12, and 14-18) (also referred to herein as a "base strap"), which may be formed from a relatively flexible piece of material, such as cloth, fabric, film, webbing, a band, and the like. While the base 138 may be configured or otherwise realized by the strap 180 as noted above and as is described in greater detail below, other configurations are contemplated, and the base 138 could be formed in other ways.

In some embodiments, the base 138 may have an elongated, generally rectangular shape, and may be operatively attached to the support frame at a first location L1 and at a second location L2 spaced from the first location L1 about the closed periphery 246. The base 138 may extend laterally between lower lateral edges of the support frame 178 to operatively attach to the support frame 178 and/or to the barrier panel 136. In some embodiments, all or a portion of the base 138 may be formed from the same material as the barrier panel 136 (e.g., the strap 180 could be manufactured from the same material as the barrier panel 136), or the base 138 could be formed from other materials. The base 138 may be operatively attached to the barrier panel 136 and/or the support frame 178 in a number of different ways, including without limitation via adhesives, stitching, bonding, welding, and the like. Other configurations are contemplated.

The base 138 is able to limit movement of the lower lateral edges of the support frame 178 away from each other to selectively place the support frame 178 in the contour frame shape SC which, as noted above, is different from the bias frame shape SB. Put differently, once in the contour frame shape SC, the base 138 limits resilient movement of the support frame 178 back toward the bias frame shape SB. Here, the base 138 exerts force adjacent to the first location L1 and the second location L2 of the support frame 178 to adjust the shape of the closed periphery 246 and the support frame 178.

Figure 4:
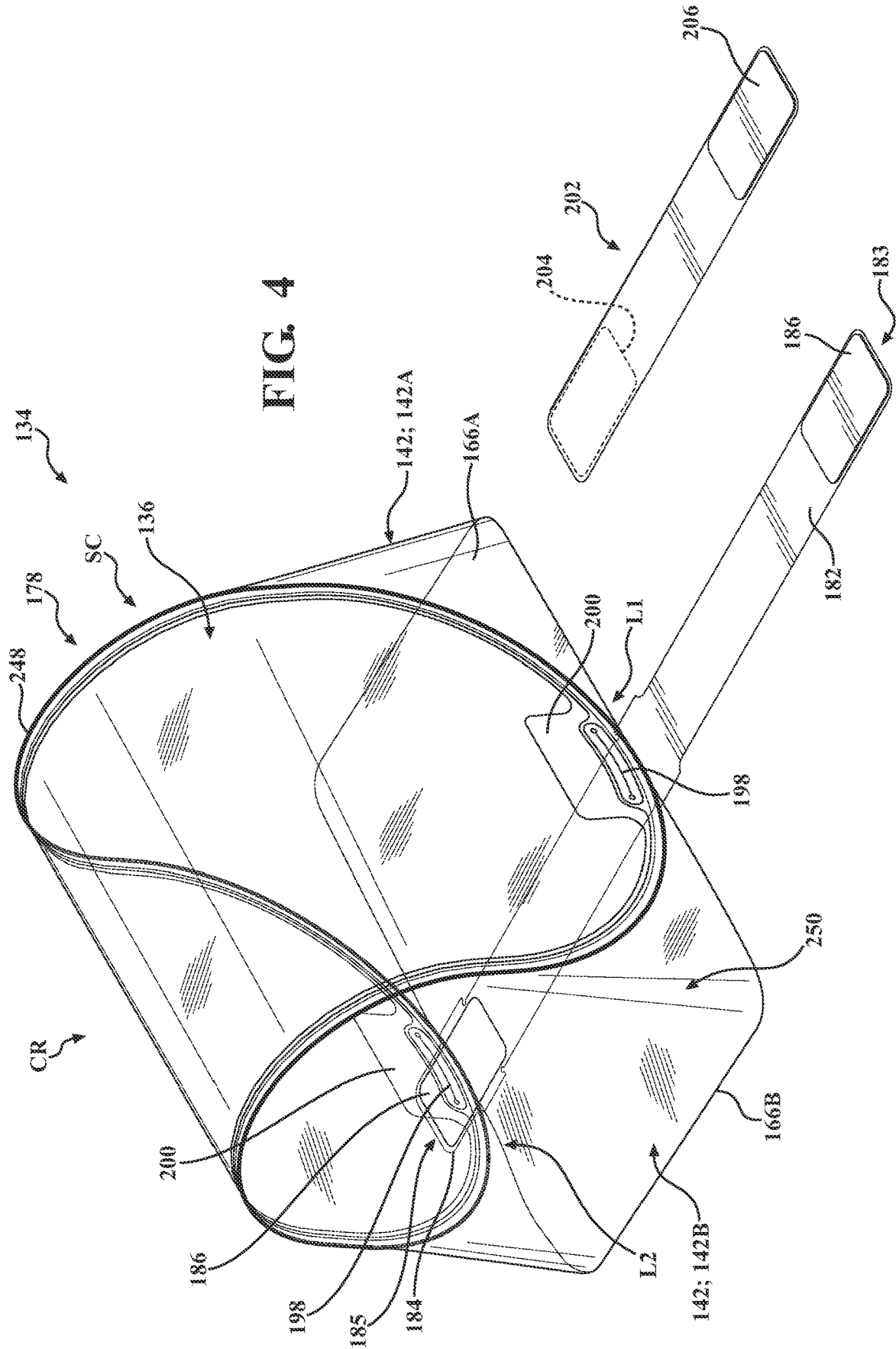
FIG. 4 is a perspective view of a shield assembly shown arranged adjacent to an extension strap, the shield assembly having a support frame in a contour frame shape, and a barrier panel, according to embodiments of the present disclosure.

As noted above, in some embodiments, the base 138 may include or otherwise be defined by a base strap 180, which extends generally between the first location L1 on the support frame 178 and the second location L2 on the support frame 178, as best shown in FIG. 4. In some embodiments, the base strap 180 may include a first retainer strap 182 (also referred to herein as a "first retainer") and a second retainer strap 184 (also referred to herein as a "second retainer"). The first retainer strap 182 extends from the first location L1 of the support frame 178 to a first retainer strap end 183, and is arranged at one lateral side of the support frame 178. The second retainer strap 184 extends from the second location L2 of the support frame 178 to a second retainer strap end 185, and is arranged at the other lateral side of the support frame 178. The first and second retainer straps 182, 184 facilitate releasably securing the shield assembly 134 to the patient support apparatus 100. The first retainer strap 182 is sized so as to be able to extend from (or otherwise be realized as a part of) the strap 180 underneath the back section 120 (or around other parts of the litter 112) to come into engagement with the second retainer strap 184. Here, in some embodiments, attachment of the first retainer strap 182 and the second retainer strap 184 together may slightly compress the mattress 124. In some embodiments, each of the retainer straps 182, 184 is provided with a fastening region, generally indicated at 186, disposed adjacent to the respective strap end. Said differently, the first retainer strap 182 has a first fastening region 186 disposed adjacent to the first retainer strap end 183 and the second retainer strap 184 has a second fastening region 186 disposed adjacent to the second retainer strap end 185. The fastening regions 186 facilitate securing the shield assembly 134 to the back section 120 of the litter 112 (see FIGS. 15 and 16). In some embodiments, anti-slip materials may be utilized on or as a part of the strap 180, the first retainer strap 182, the second retainer strap 184, and/or other portions of the base 138.

In some embodiments, the fastening regions 186 may each comprise one of a hook fastening material and a loop fastening material. Said differently, one of the first fastening region 186 of the first retainer strap 182 and the second fastening region 186 of the second retainer strap 184 may comprise a hook fastening material, and the other of the first fastening region 186 of the first retainer strap 182, and the second fastening region 186 of the second retainer strap 184 comprises a loop fastening material. The hook fastening material and the loop fastening material are configured to releasably engage one another to couple the first retainer strap 182 to the second retainer strap 174. Other materials that are engageable to facilitate removable coupling are contemplated. It will be appreciated that the second retainer strap 184 could be omitted in some embodiments, such as where a portion of a corresponding hook or loop fastening material releasably engageable with the fastening region 186 is provided on the outer surface of the barrier panel 136, the support frame 178, or other portions of the shield assembly 134. However, it will be appreciated that other configurations are contemplated, and the shield assembly 134 could utilize other types first and second retainer straps 182, 184. By way of non-limiting example, in the representative embodiment illustrated in FIG. 17, the shield assembly 134 utilizes first and second retainer straps 182, 184 which each comprise respective straps with hooks 188 that are configured to engage portions of the back section 120 of the litter 112 (or other locations of the patient support apparatus 100) to secure the shield assembly 134 to the patient support apparatus 100. It will be appreciated that the first and second retainer straps 182, 184 could be realized with various materials, including elastic materials. Similarly, the hooks 188 could be of various sizes, shapes, and/or configurations.

Figure 16:
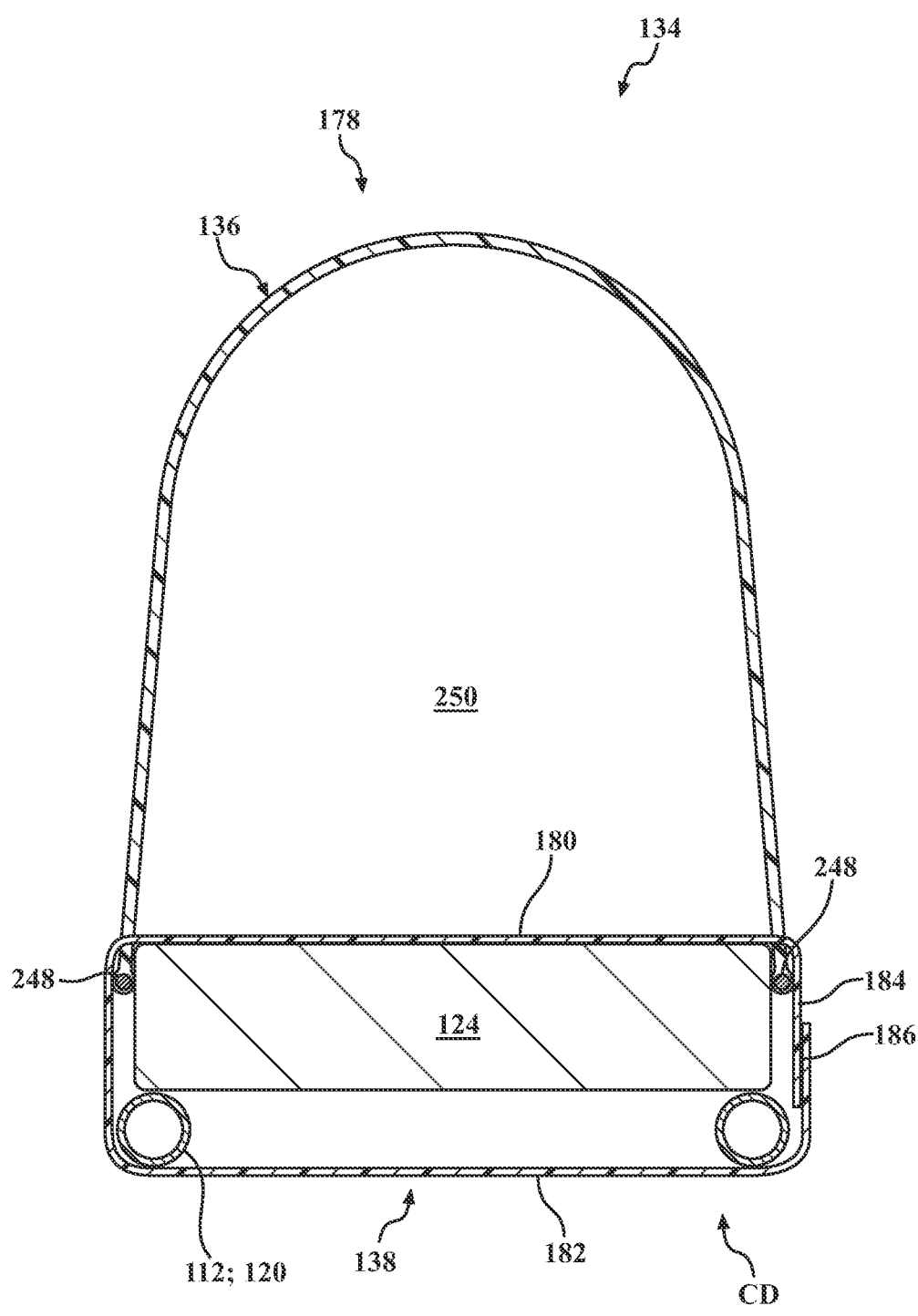
FIG. 16 is a partial slice section view taken along line 16-16 in FIG. 15, shown with the first retainer strap extending laterally beneath the back section and attached to the second retainer strap via a hook-and-loop fastener arrangement.
Figure 17:
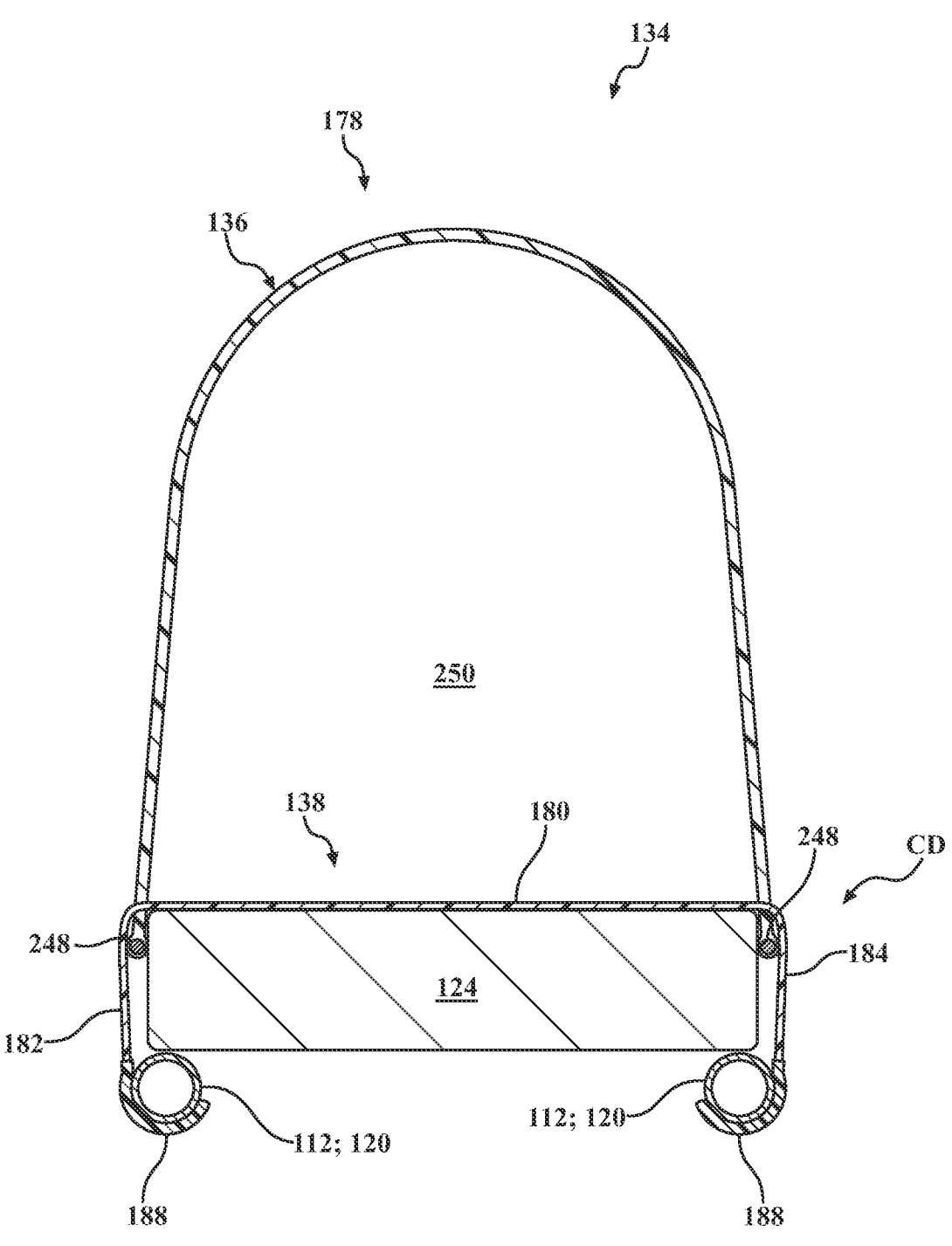
FIG. 17 is a partial slice section view of another embodiment of a shield assembly according to the present disclosure, shown with a first retainer strap realized as a hook attached to one lateral side of a back section of a litter, and with a second retainer strap realized as another hook attached to another lateral side of the back section to secure the shield assembly to the litter.
Figure 18:
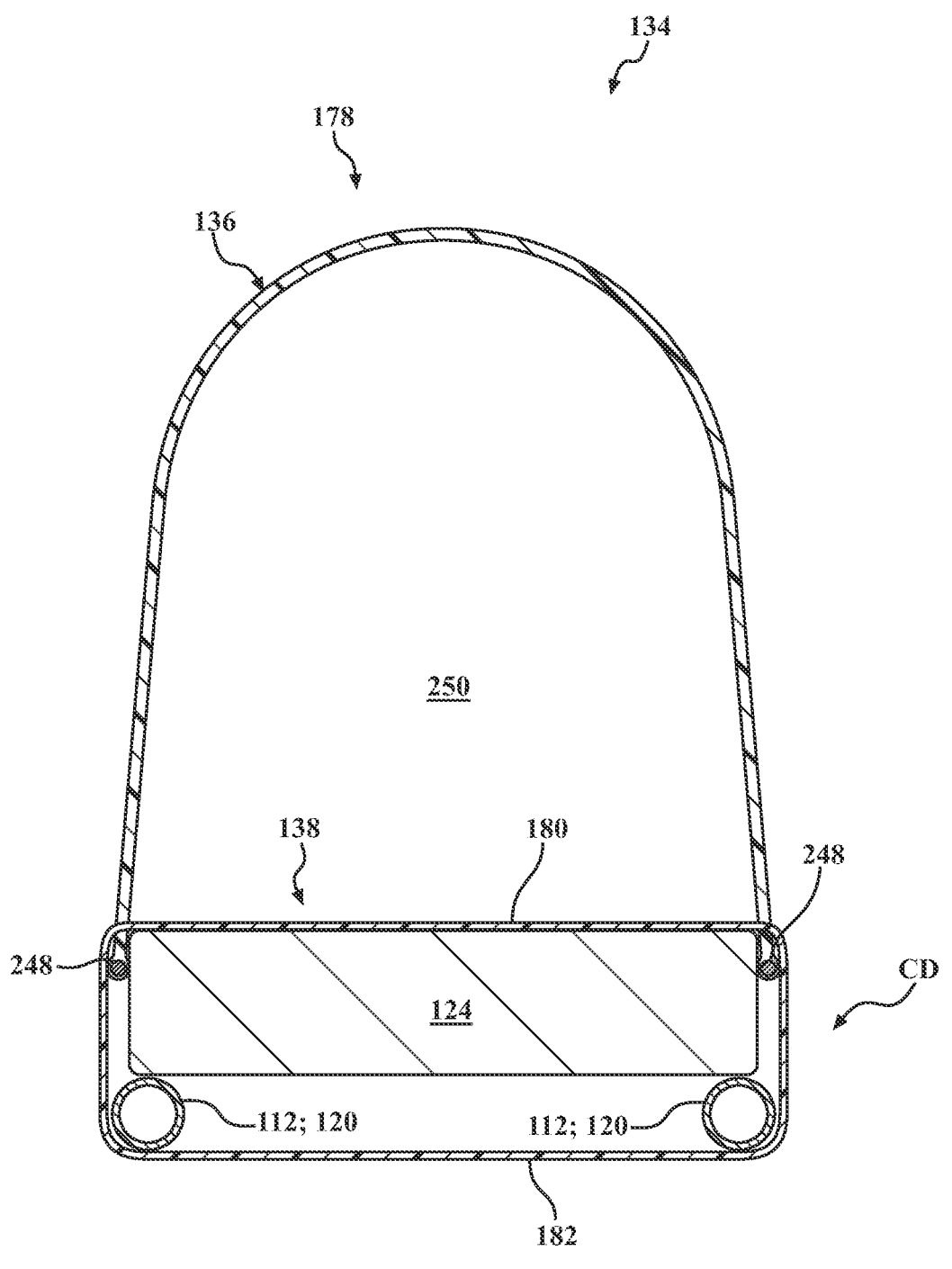
FIG. 18 is a partial slice section view of another embodiment of a shield assembly according to the present disclosure, shown with a retainer strap of the shield assembly stretched around a back section and a portion of a mattress of a litter to secure the shield assembly to the litter.

FIG. 18 shows another embodiment of the shield assembly 134 that is similar to the embodiment depicted in FIG. 16. However, in this embodiment, a single retainer 182 is utilized which extends in a closed loop as a part of the strap 180 defining the base 138. Here, the retainer 182 may be formed from an elastic (or tension-able) material that is slid onto the back section 120 of the litter 112. However, other configurations are contemplated.

Figure 19:
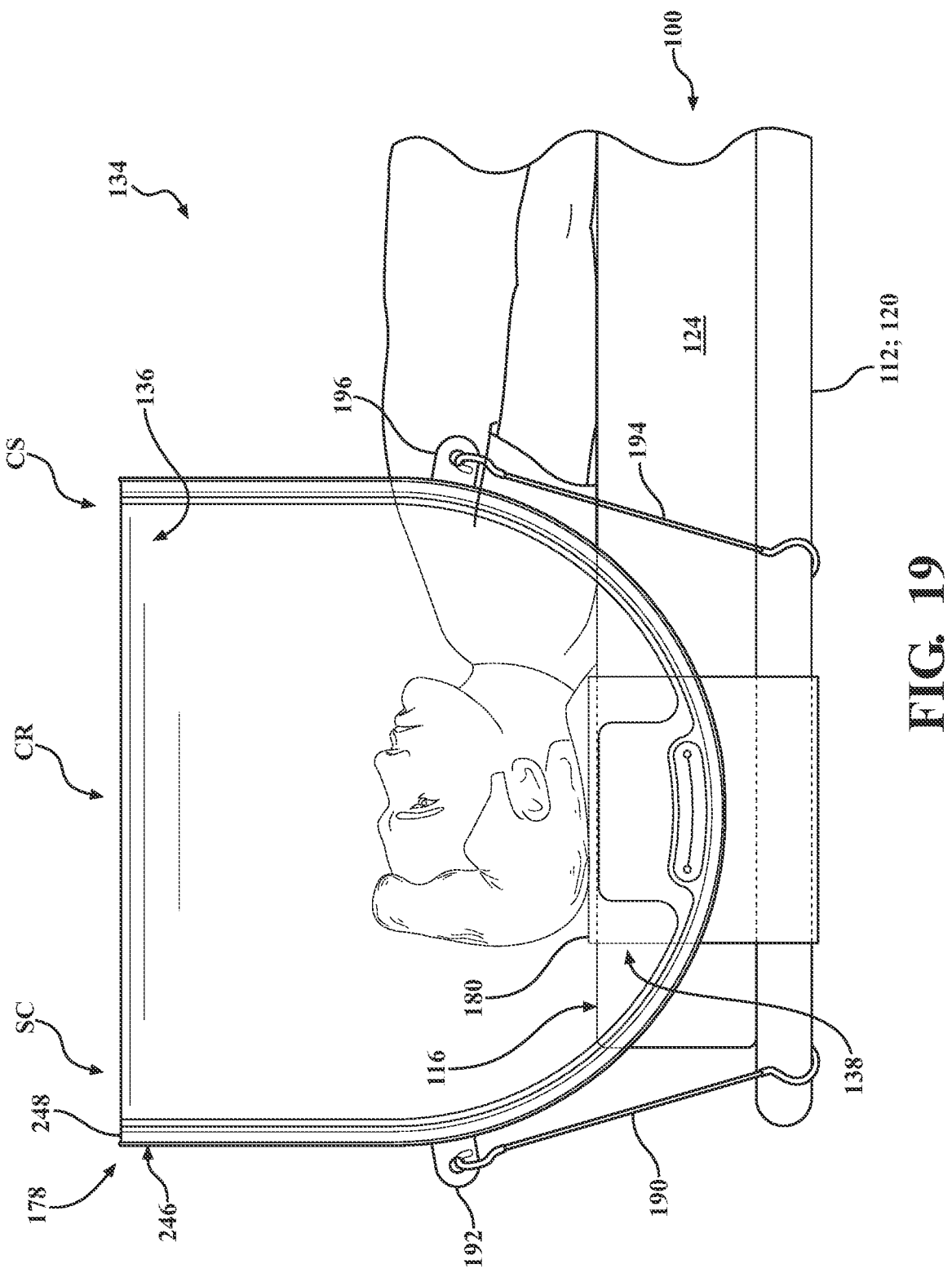
FIG. 19 is a partial side view of a litter to which a shield assembly is secured according to embodiments of the present disclosure, shown with first and second keepers coupled to and extending between the shield assembly and the litter to arrange the shield assembly in a secured configuration.
Figure 20:
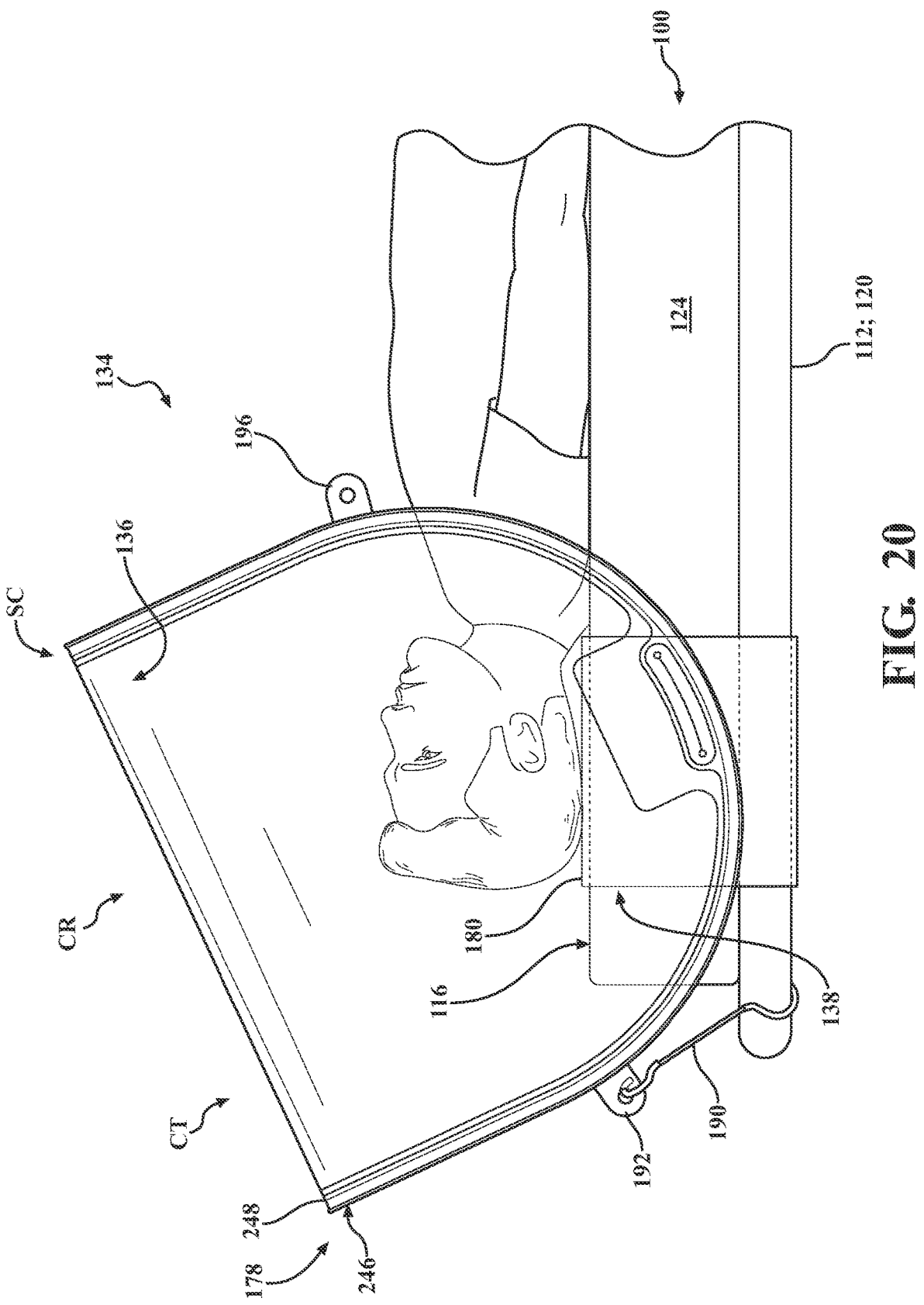
FIG. 20 is another partial side view of the litter and the shield assembly of FIG. 19, shown with the first keeper coupled to and extending between the shield assembly and the litter to arrange the shield assembly in a tilted configuration.
Figure 21:
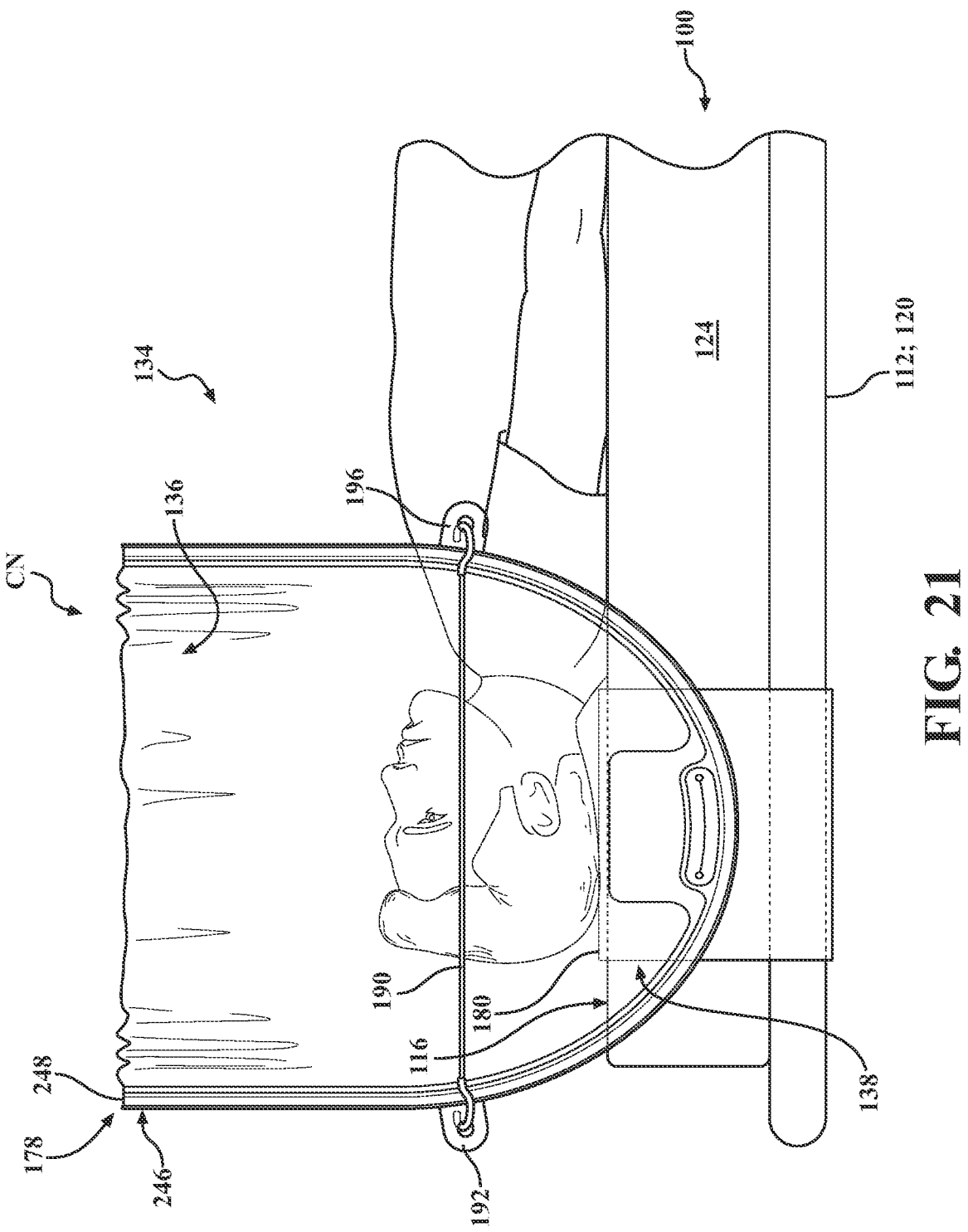
FIG. 21 is a partial side view of a litter and a shield assembly according to embodiments of the present disclosure, shown with a keeper coupled to opposing longitudinal sides of the shield assembly to arrange the shield assembly in a cinched configuration.

FIG. 19 depicts a first keeper 190 attached to the back section 120 and to a first mounting point 192 (depicted schematically) of the shield assembly 134 arranged adjacent to the proximal end, and a second keeper 194 attached to the back section 120 and to a second mounting point 196 (depicted schematically) of the shield assembly arranged adjacent to the distal end. Here, the first and second mounting points 192, 196 could be realized as parts of the support frame 178, as portions of the barrier panel 136, or as other discrete components or regions formed as a part of or otherwise operatively attached to the shield assembly 134. Here in FIG. 19, the first and second keepers 190, 194 (as well as other keepers) may be utilized to help maintain or otherwise control the position the shield assembly 134 on the litter 112. To this end, the schematically-depicted first and second keepers 190, 194 comprise elastic bands with hooks that can attach to the back section 120, to other parts of the litter 112, to the first and/or second mounting points 192, 196, and/or to various parts of the shield assembly 134 in order to secure the shield assembly 134 to the patient support apparatus 100. FIG. 20 is similar to FIG. 19, but shows the second keeper 194 having been removed, such as to arrange the shield assembly 134 in a tilted configuration CT. FIG. 21 is likewise similar to FIG. 20, but shows the first keeper 190 coupled to both the first and second mounting points 192, 196 to arrange the shield assembly 134 in a cinched configuration CN. Here, it will be appreciated that multiple keepers 190, 194 could be used, arranged similarly or in other ways (e.g., at the top distal and proximal edges of the support frame 178) to arrange the shield assembly 134 in the cinched configuration CN.

As noted above, when the base 138 holds the support frame 178 in the contour frame shape SC, the adjustment (or "deformation") of the support frame 178 effects tension in the resilient element 248 and transforms the closed periphery 246 to place the barrier panel 136 in the curved configuration CR which defines the patient accommodation space 250 shaped to receive the patient adjacent to the base 138 and to the barrier panel 136. In some embodiments, the contour frame shape SC of the support frame 178, and the curved configuration CR of the barrier panel 136, may be realized with a generally hyperbolic paraboloid profile or configurations such that the barrier panel 136 approximates a hyperbolic paraboloid or similar shape (e.g., a curved section with an approximately constant radius). In some embodiments, the base 138 may comprise a generally trapezoidal profile to, among other things, adjust the shape of the shield assembly 134 so as to be "wider" at one longitudinal end. In some embodiments, the base 138 may comprise multiple components, such as two or more longitudinally-spaced pieces of material, straps, webbing, and the like. Other configurations are contemplated.

Figure 6:
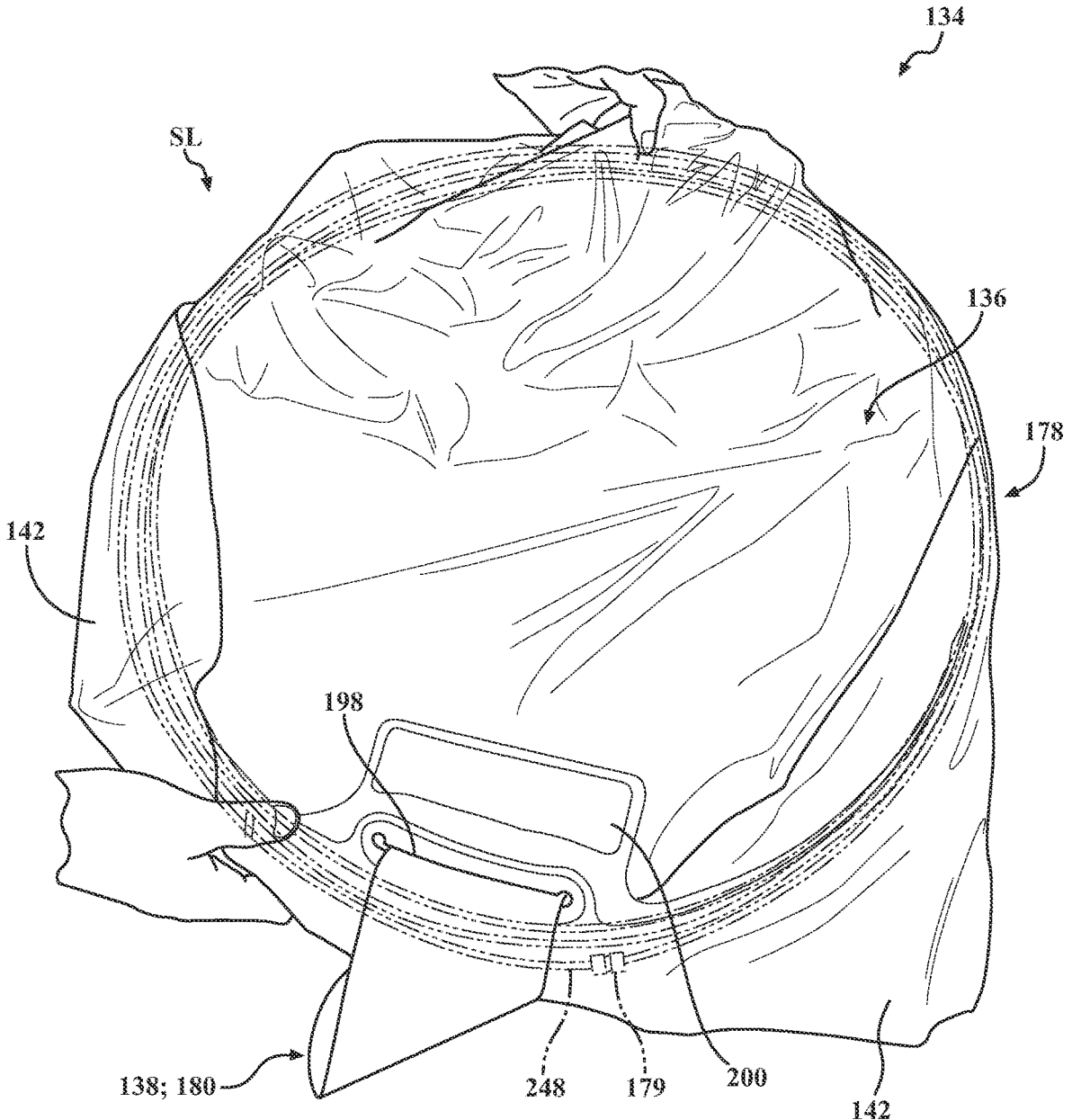
FIG. 6 is a perspective view of the shield assembly of FIGS. 1-5, shown with the support frame arranged in a collapsed frame shape.

As shown FIG. 6, in some embodiments, the support frame 178 is configured so as to be selectively adjustable from the contour frame shape SC to a collapsed frame shape SL. Here, the resilient element 248 of the shield assembly 134 is configured so as to facilitate being twisted over itself (e.g., in a collapsed "figure eight" shape). The resilient element 248 can be twisted in such a way so as to reduce the overall size of the shield assembly 134, such as to reduce the overall size of the shield assembly 134 for shipping and/or storage prior to use, which may allow the shield assembly 134 to be stowed in a caregiver's trauma kit, in a bag, or in other suitable locations. In some embodiments, a strap, band, pouch, sealed container, and like could be utilized to keep the shield assembly 134 in the collapsed configuration. Once needed, the shield assembly 134 can be "unfolded" and secured to or otherwise placed upon the patient support apparatus 100, as described in greater detail below.

Figure 22:
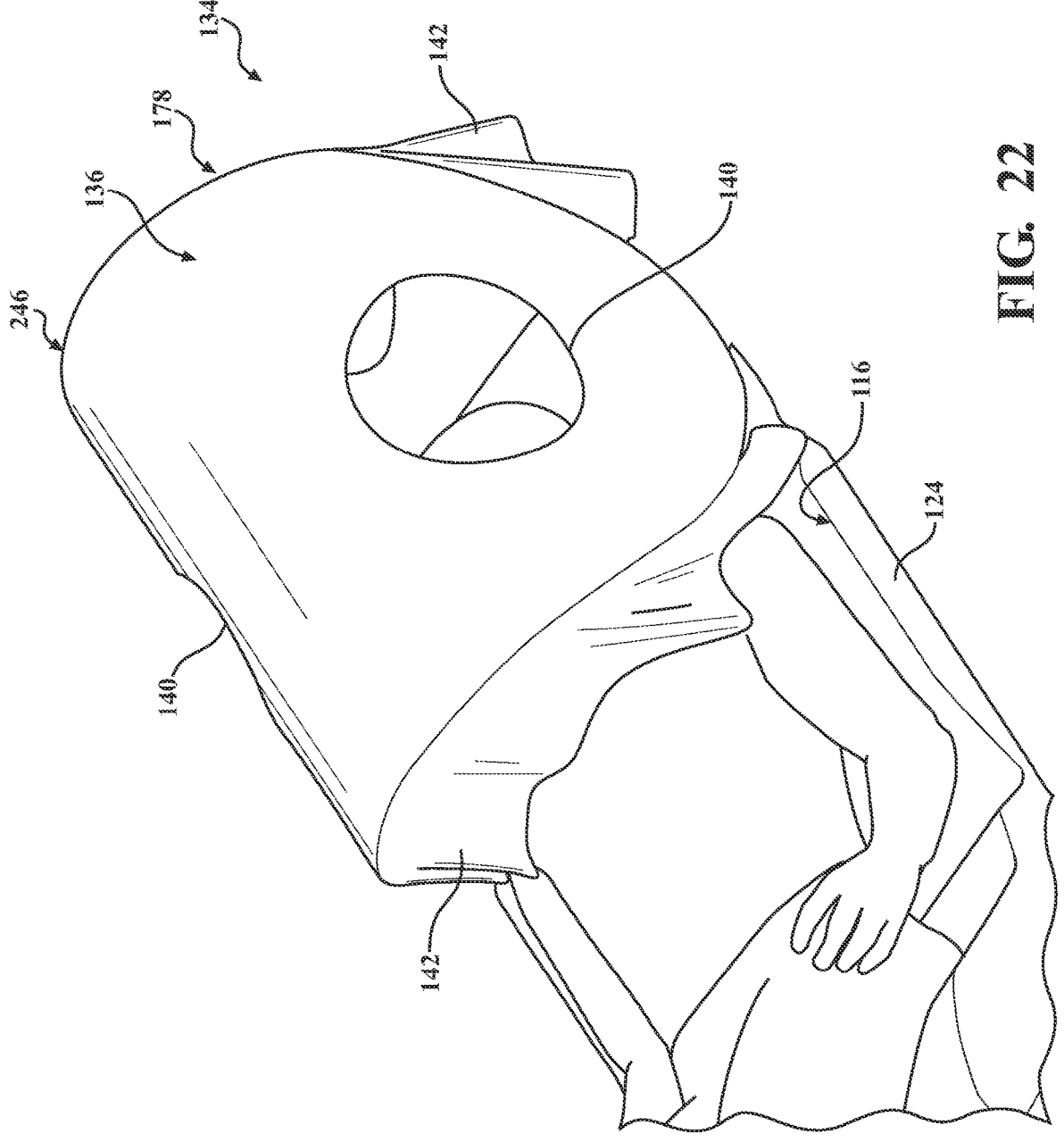
FIG. 22 is a partial perspective view of a back section of a litter to which a shield assembly is secured, according to embodiments of the present disclosure.

As noted above, in some embodiments, the barrier panel 136 and/or other portions of the shield assembly 134 may be formed from multiple materials, some of which may be substantially transparent (e.g., "clear"), semi-transparent (e.g., "frosted" and/or "tinted"), and/or non-transparent (e.g., opaque). Where multiple materials are utilized, the different components or materials may be coupled together and/or to other portions of the shield assembly 134 in various ways (e.g., by bonding, adhesives, plastic welding, and the like). In some embodiments, such as is depicted in FIG. 22, one portion of the barrier panel 136 may comprise a semi-transparent (or non-transparent) material (e.g., the portion of the barrier panel 136 which engages the support frame 178), and another portion of the barrier panel 136 may comprise a substantially transparent material, such as to form one or more windows 140. Here, the portion of material forming the window 140 shown in FIG. 22 may be bonded to the other portions of the barrier panel 136 as noted above. Other configurations are contemplated, and it will be appreciated that windows 140 could be provided in various locations and quantities, with various profiles, shapes and arrangements, without departing from the scope of the present disclosure. In some embodiments, the windows 140 could instead be realized as "ports" to facilitate caregiver access to the patient, and may be covered such as with flaps of other material, or removable material panels (not shown). In some embodiments, gloves or other handling barriers (not shown) could be supported within the windows 140 and coupled to the barrier panel 136 to allow the caregiver to maintain the barrier with the patient while administering care. As is described in greater detail below in connection with FIGS. 12-13, windows 140 could also be used to promote line management (e.g., tubing for air and/or liquids, electrical lines, sensors, and the like). Other configurations are contemplated.

As noted above, in some embodiments, the shield assembly 134 may comprise one or more drape panels 142, arranged such as at longitudinal ends of the barrier panel 136 (e.g., a proximal end or a distal end of the barrier panel 136). To this end, a drape panel 142 may be coupled to the support frame 178 and extend away from the closed periphery 246 to a drape edge 166 to define a draped area 168. The draped area 168 is in communication with the patient accommodation space 250 when the support frame 178 is disposed in the contour frame shape SC. In some embodiments, such as is depicted in FIGS. 1-13, the shield assembly 134 may comprise more than one drape panel 142. For example, the shield assembly 134 may comprise a first drape panel 142A and a second drape panel 142B. The first drape panel 142A may be arranged at a distal end of the shield assembly 134, or toward the head end of the patient support apparatus 100. The second drape panel 142B may be arranged at the proximal end of the shield assembly 134, or toward the foot end of the patient support apparatus 100.

More specifically, in some embodiments the first drape panel 142A may be coupled to the support frame 178 and extend away from the closed periphery 246 to a first drape edge 166A to define a first draped area 168A in communication with the patient accommodation space 250 when the support frame 178 is disposed in the contour frame shape SC. Similarly, the second drape panel 142B may be coupled to the support frame 178 and extend away from the closed periphery 246 to a second drape edge 166B to define a second draped area 168B in communication with the patient accommodation space 250 when the support frame 178 is disposed in the contour frame shape SC. Here, the drape panels 142 provide additional barriers without substantially restricting access to the patient.

It will be appreciated that the barrier panel 136 and/or the drape panels 142 may be formed from a single material, or from multiple materials. Other configurations are contemplated. In some embodiments, the first drape panel 142A (e.g., arranged adjacent to the head end) may comprise a relatively transparent material, and the second drape panel 142B (e.g., arranged extending towards the foot end) may comprise a semi-transparent (e.g., "frosted") or non-transparent material. In some embodiments, lower edges 166A, 166B of the drape panels 142A, 142B may be provided with weights, fasteners, magnets, attachment points, and the like to help shape or otherwise control how the drape panel 142 lays during use. In some embodiments, such as described in greater detail below in connection with FIGS. 7-11, one of the drape panels 142A, 142B may be larger (e.g., laterally "wider") and/or longer than the other drape panel 142A, 142B. For example, in the embodiment shown in FIG. 7, the first drape panel 142A is larger than the second drape panel 142B in multiple directions to define a larger surface area that can be positioned about the end of a relatively wide mattress 124 (see also FIG. 11). Other configurations are contemplated.

When materials having different transparency or opacity levels are used for the barrier panel 136 and the drape panels 142A, 142B, the portions of the shield assembly 134 that have similar transparency levels may cooperate to define a window portion 252 of the of the shield assembly 134 to promote visibility through the barrier, or a privacy portion 254 to limit visibility through the barrier. For example, the barrier panel 136 and the first drape panel 142A may cooperate to define the window portion 252 of the shield assembly 134 when the barrier panel 136 and the first drape panel 142A are both formed from a substantially transparent material. Similarly, the second drape panel 142B may define the privacy portion 254 when it is formed from a semi-transparent or non-transparent material. It should be appreciated that the barrier panel 136 and/or the drape panels 142A, 142B could each be formed from substantially transparent materials, semi-transparent materials, non-transparent materials, and/or combinations thereof.

Figure 5:
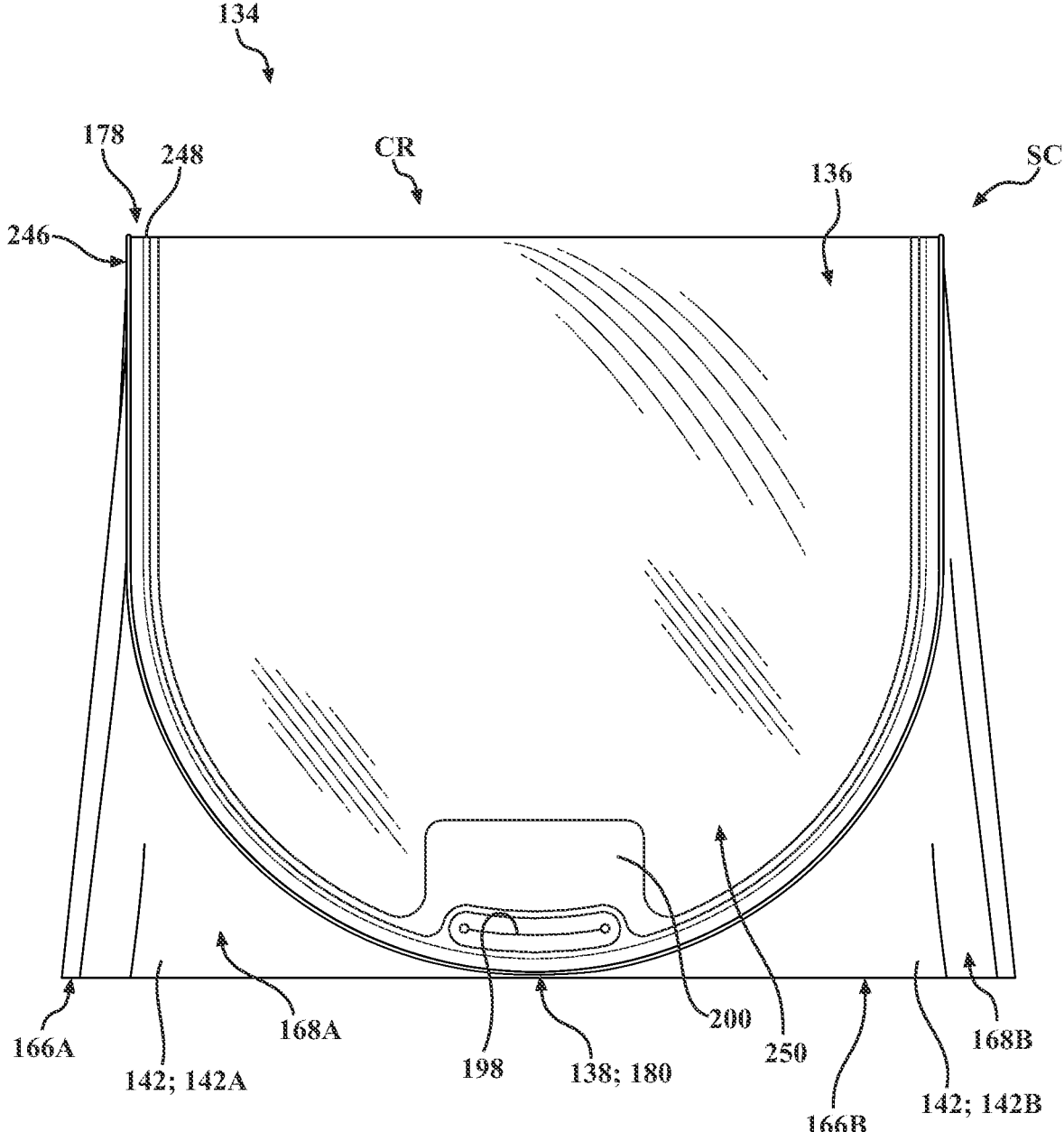
FIG. 5 is a side view of the shield assembly of FIG. 4.

Referring now to FIGS. 1-13, embodiments of shield assemblies 134 are shown which are configured with the strap 180 as a part of or otherwise defining the base 138. As is best depicted in FIGS. 4-6, the strap 180 may be configured to extend from one lateral side of the support frame 178 to the other lateral side of the support frame 178 to define the base 138, which can be placed on top of the mattress 124 underneath the patient in a deployed configuration CD. Here, strap slots 198 are formed in the barrier panel 136 adjacent to the first and second locations L1, L2 near lower portions of the support frame 178, to facilitate routing the strap 180 as well as tensioning/adjusting the strap 180 to accommodate differently-sized and/or shaped mattresses 124, litters 112, and the like. The strap slots 198 are shaped to receive the strap 180 therethrough, such that the strap 180 extends through the strap slots 198 away from the patient accommodation space 250. The strap slots 198 are configured such that the support frame 178 can be adjusted from the collapsed frame shape SL (see FIG. 6) and "unfolded" or otherwise released before passing the strap 180 through at least one of the strap slots 198 to adjust the support frame 178 into the contour frame shape SC with the barrier panel 136 in the curved configuration CR (e.g., the generally hyperbolic paraboloid profile/shape) and thereby place the shield assembly 134 in the deployed configuration CD.

In some embodiments, the barrier panel 136 may be provided with reinforced regions 200 adjacent to or otherwise surrounding the strap slots 198. More specifically, the barrier panel 136 may include a first reinforced region 200 arranged adjacent to the first location L1 of the support frame 178, with the first strap slot 198 formed in the first reinforced region 200; and the barrier panel 136 may further include a second reinforced region 200 arranged adjacent to the second location L2 of the support frame 178, with the second strap slot 198 formed in the second reinforced region 200. The reinforced regions 200 may be formed in a variety of ways, such as by attaching a second layer of material formed from the same as the barrier panel 136 on top of the barrier panel 136 near the first and second locations L1, L2, by reforming the material, and the like. Alternatively, a different material may be used, such as a material that is thicker and to provide increased strength and resistance to tearing. Other configurations are contemplated.

In order for the shield assembly 134 to be secured to the patient support apparatus 100, the strap 180 can be routed around the mattress 124 and the back section 120 of the litter 112 to bring the first and second retainer straps 182, 184 into engagement with each other. To this end, hook and loop fastening regions 186 may be employed as noted above, but other configurations are contemplated (e.g., adjustable web-
bing, releasable interlocking mechanical connectors, straps
that can be "tied-off" or otherwise secured, and the like). In
some embodiments, the first and second retainer straps 182,
184 may be sized, shaped, or otherwise arranged so as to
promote adjustability of the "tension" placed on the mattress
124 between the base 138 and the strap 180, as the strap 180
is routed around the support frame 178 (which may be
indirectly abutting the mattress 124). It will be appreciated
that this configuration can help promote utilization of the
shield assembly 134 with different types of patient support
apparatuses 100 (e.g., having wider or narrower litters 112,
back sections 120, and the like), as well as patient transfer
between different patient support apparatuses 100 (see FIG.
2). For example, the shield assembly 134 can be attached to
one patient support apparatus 100 with the first and second
retainer straps 182, 184 engaging each other to secure to the
mattress 124 on the back section 120, and the first and
second retainer straps 182, 184 could be subsequently
released to place the shield assembly 134 to facilitate patient
transfer to another patient support apparatus 100 (e.g., a
stretcher as shown in FIG. 2). Once on the other patient
support apparatus 100, the first and second retainer straps
182, 184 could be subsequently re-attached to each other to
secure the shield assembly 134 to the patient support appa-
ratus 100. It will be appreciated that patient transfer can be
accomplished in this way without necessitating that the
shield assembly 134 be removed or stowed because the
shield assembly 134 can be moved concurrently with the
patient.

Referring now to FIG. 7, in some embodiments, an
extension strap 202 with auxiliary first and second retainers
204, 206 may be provided to "lengthen" the strap 180, such
as to accommodate patient support apparatuses 100 with
relatively wide litters 112, back sections 120, mattresses
124, and the like (see also FIG. 4). Here, one or more
auxiliary first auxiliary retainers 204 and/or one or more
auxiliary second retainers 206 could be arranged, sized,
and/or shaped in various ways along the extension strap 202
to accommodate or otherwise improve adjustability, routing,
handling, and the like. Other configurations are contem-
plated. In some embodiments, the auxiliary first retainer 204
and/or the auxiliary second retainer 206 may employ hook
and loop fastening regions 186 (not shown in detail) similar
to as described above. Other configurations are contem-
plated.

Referring now to FIGS. 7-10, in some embodiments, the
shield assembly 134 is provided with one or more types of
keepers 190, 194 to facilitate securing the shield assembly
134 to the litter 112 or another part of the patient support
apparatus 100). Here, it will be appreciated keepers 190, 194
may be used in addition to the first and second retainer straps
182, 184 in some embodiments, or may be utilized without
the first and second retainer straps 182, 184. In scenarios
where the patient has been transferred to (or has otherwise
been positioned on) a patient support apparatus 100 with a
relatively wide mattress 124 (e.g., a stretcher as shown in
FIG. 2), it may be advantageous to secure the shield assem-
bly 134 to the litter 112 or to another part of the patient
support apparatus 100 utilizing keepers 190, 194 without
also attaching the first and second retainer straps 182, 184
together. Here, it may be difficult for a caregiver to route the
first and second retainer straps 182, 184 around the mattress
124 in certain situations, with or without utilizing an exten-
sion strap 202. This type of difficulty may occur based on the
dimensions of the mattress 124, the construction of the
patient support apparatus 100, a lack of clearance below the litter 112, and the like. In any event, it will be appreciated
that the shield assembly 134 can nevertheless be secured to
the patient support apparatus 100 by utilizing keepers 190,
194 of various types, styles, and/or configurations, without
requiring that the first and second retainer straps 182, 184 be
attached together in some embodiments.

Figure 8:
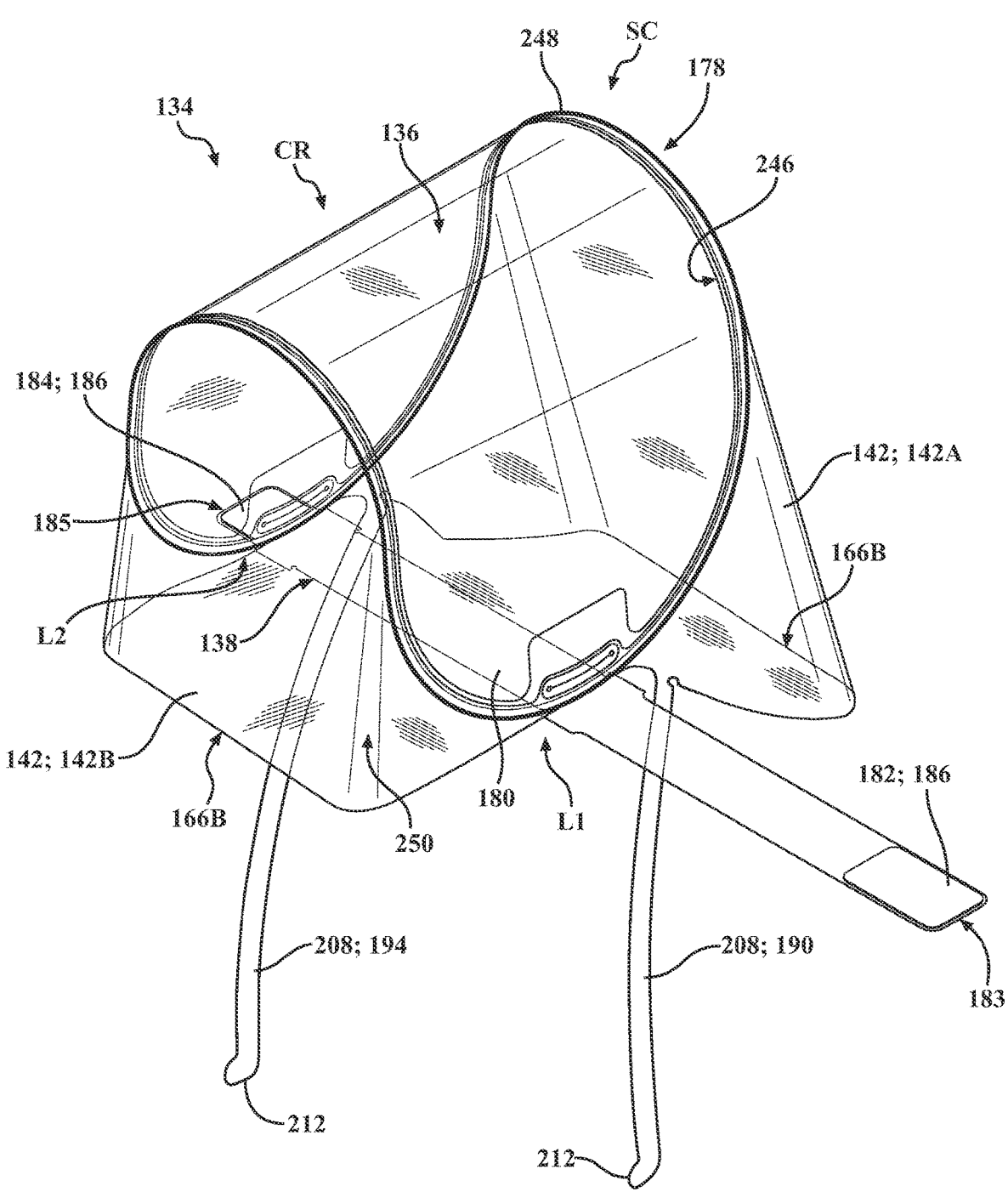
FIG. 8 is a perspective view of the shield assembly of FIG. 7 shown with the support frame arranged in a contour frame shape, and depicting the drape straps coupled to the first drape having been defined via separation along the perforated paths.
Figure 9:
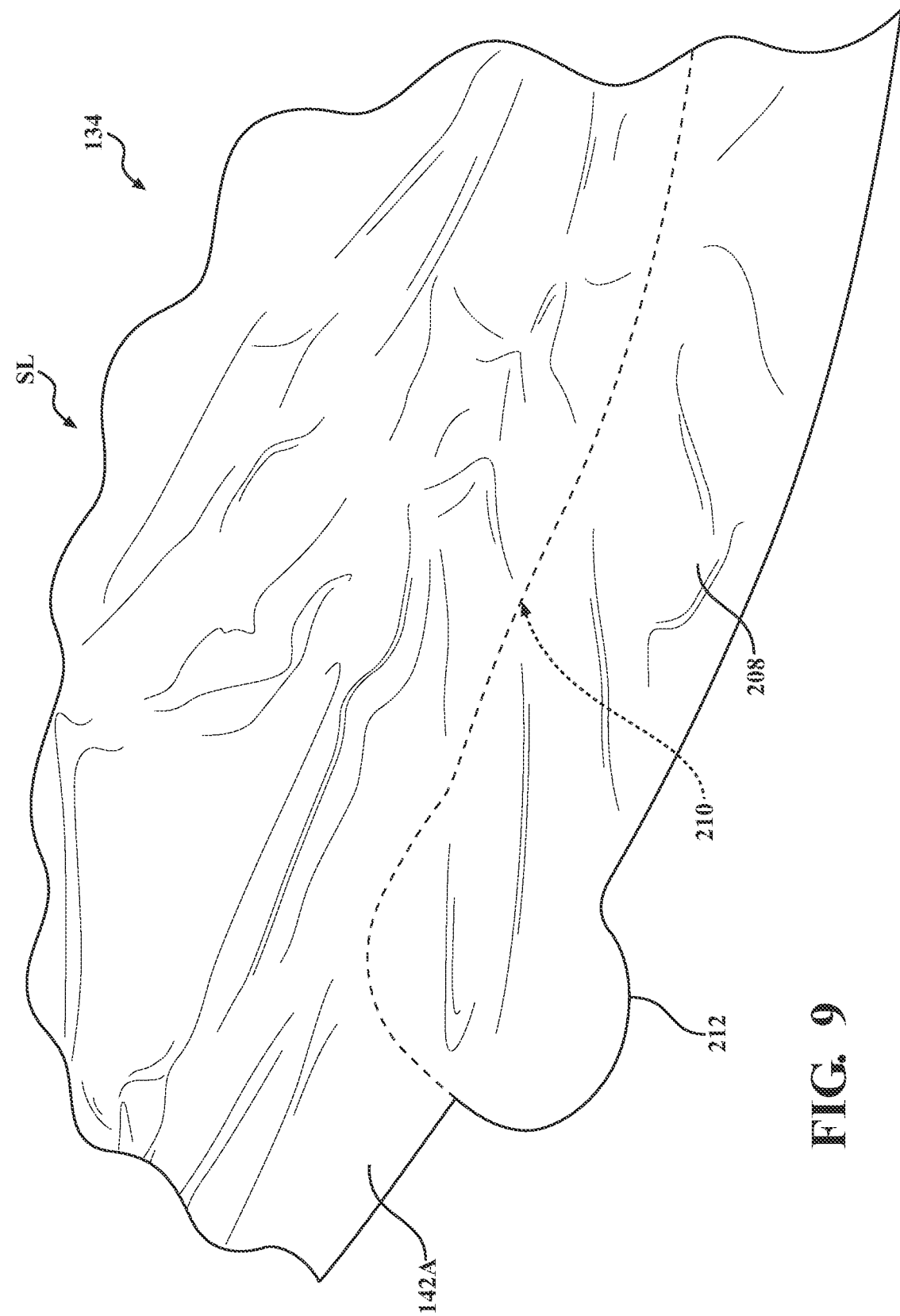
FIG. 9 is a partial perspective view of another shield assembly and depicting portions of the first drape and one of the drape straps prior to separation along one of the perforated paths.
Figure 10:
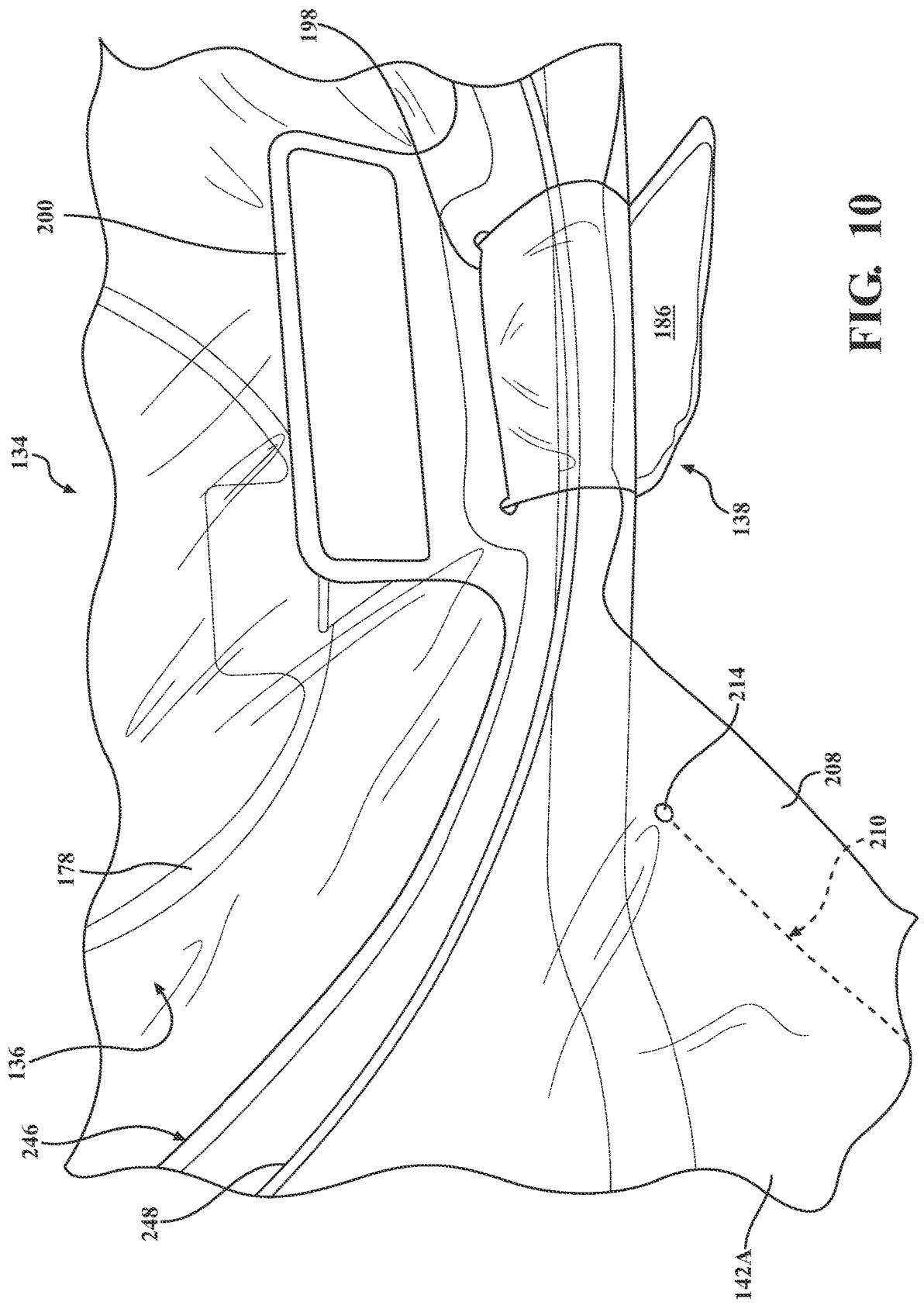
FIG. 10 is another partial perspective view of the shield assembly of FIG. 9, depicting additional portions of the first drape and one of the drape straps prior to separation along one of the perforated paths.
Figure 11:
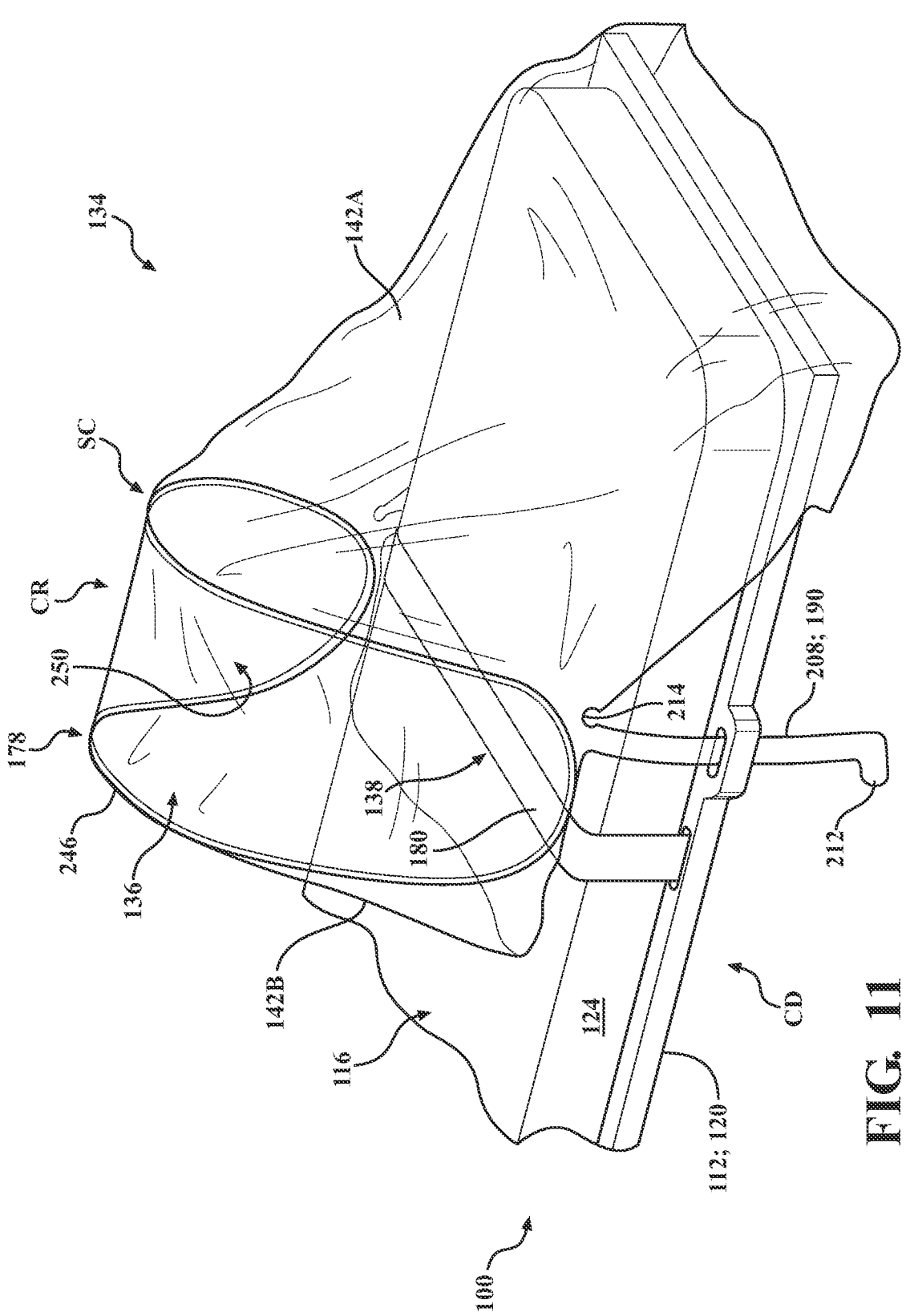
FIG. 11 is another perspective view of the shield assembly of FIGS. 9 and 10, shown arranged on a patient support apparatus with one of the drape straps coupled to the first drape having been defined by separation along one of the perforated paths, with the drape strap depicted passing through a portion of the patient support apparatus to illustrate the process of securing the shield assembly to the patient support apparatus.

In some embodiments, such as the embodiment illustrated
in FIGS. 7-11, the shield assembly 134 may include one or
more keepers 190, 194 realized as drape straps 208 that are
operatively attached to the drape panel 142 (e.g., the first
drape panel 142A). Here, the drape straps 208 are defined
along perforated paths 210 formed adjacent to the drape
edge 166A of the first drape panel 142A. In embodiments
having only one drape strap 208, the drape strap 208 may be
arranged at a longitudinal end of the first drape panel 142A,
while embodiments having two drape straps 208, such as
shown in FIGS. 7-8, a first drape strap 208 may be arranged
on a first lateral side of the drape panel 142A and a second
drape strap 208 may be arranged on a second lateral side of
the drape panel 142A. The drape straps 208 are arranged so
as to facilitate releasably securing the drape panel 142A, and
thus the shield assembly 134 generally, to the patient support
apparatus 100. Here, the drape straps 208 each have a pull
tab 212 disposed adjacent to the drape edge 166A and
arranged for engagement by a user to facilitate tearing along
the perforated paths 210 away from the drape panel 142A
and up to a transition relief 214.

It will be appreciated that "tearing" along the perforated
paths 210 defines the drape straps 208, which remain con-
nected to the drape panel 142. Once defined, the drape straps
208 can be utilized to secure the shield assembly 134 to the
patient support apparatus 100, such as by "tying" the drape
straps 208 to the litter 112 (or another part of the patient
support apparatus 100). However, it will be appreciated that
other configurations are contemplated by the present disclo-
sure, and the drape straps 208 could be configured in other
ways, such as with various types of keepers 190, 194
comprising arrangements of hooks, clasps, and the like.
While the drape straps 208 are thus formed integrally with
the first drape panel 142A in the illustrated embodiment, it
will be appreciated that the drape straps 208 (and/or other
types of keepers 190, 194) may be operatively attached to
(or otherwise formed integrally with) the first drape panel
142A in a number of different ways. Similarly, drape straps
208 may be provided at the second drape panel 142B, and/or
along other portions of the shield assembly 134. Other
configurations are contemplated.

Figure 12:
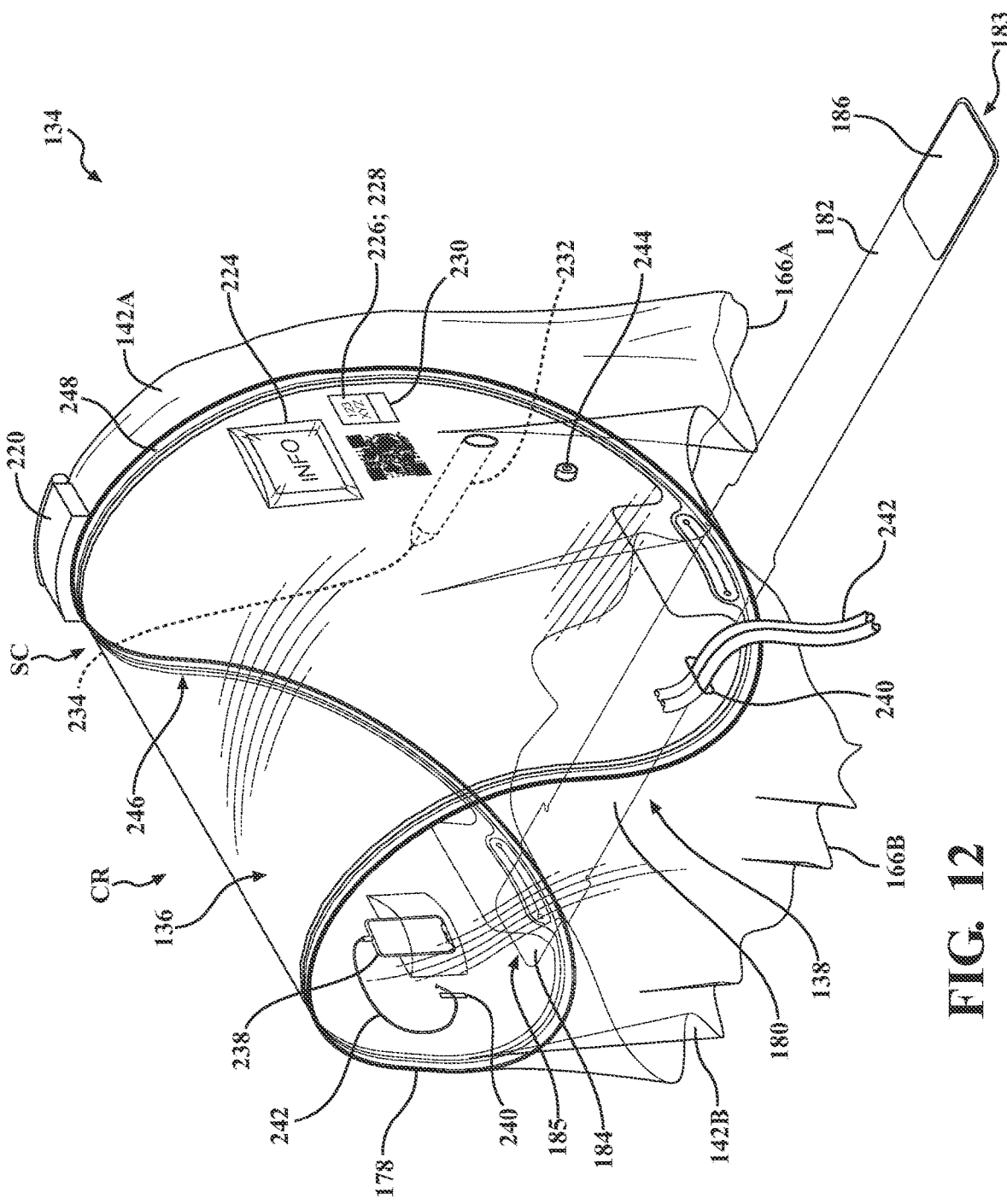
FIG. 12 is a perspective view of a shield assembly according to embodiments of the present disclosure, shown including first and second drapes and a barrier panel operatively attached to a support frame coupled to a base, and shown with a pouch coupled to the support frame to retain an auxiliary drape panel.
Figure 13:
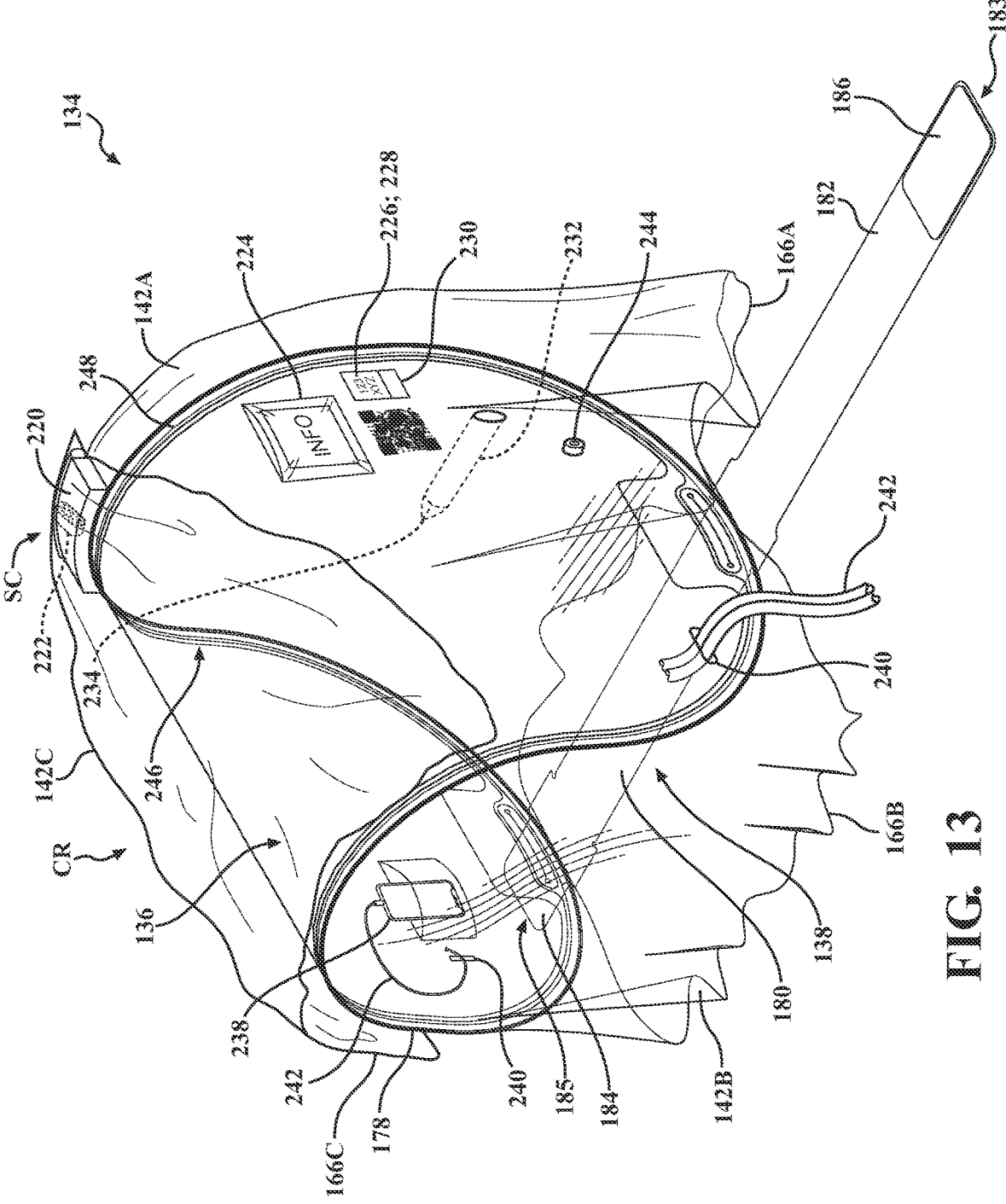
FIG. 13 is another perspective view of the shield assembly of FIG. 12, shown with the auxiliary drape panel arranged extending from the pouch over the barrier panel.
Figure 14:
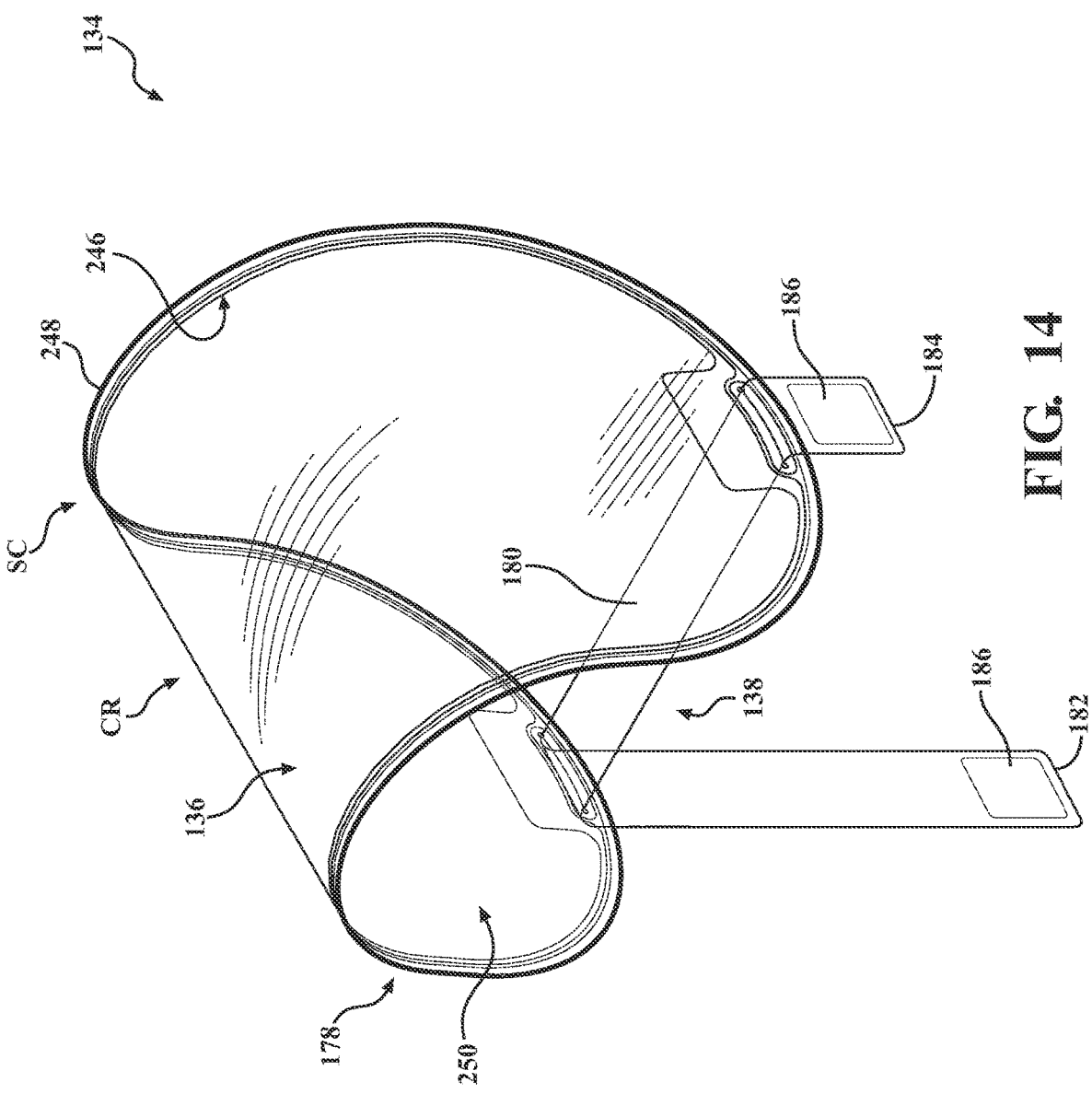
FIG. 14 is a perspective view of a shield assembly shown having a barrier panel supported by a support frame attached to a base having a first retainer strap and a second retainer strap spaced from the first retainer strap according to embodiments of the present disclosure.
Figure 15:
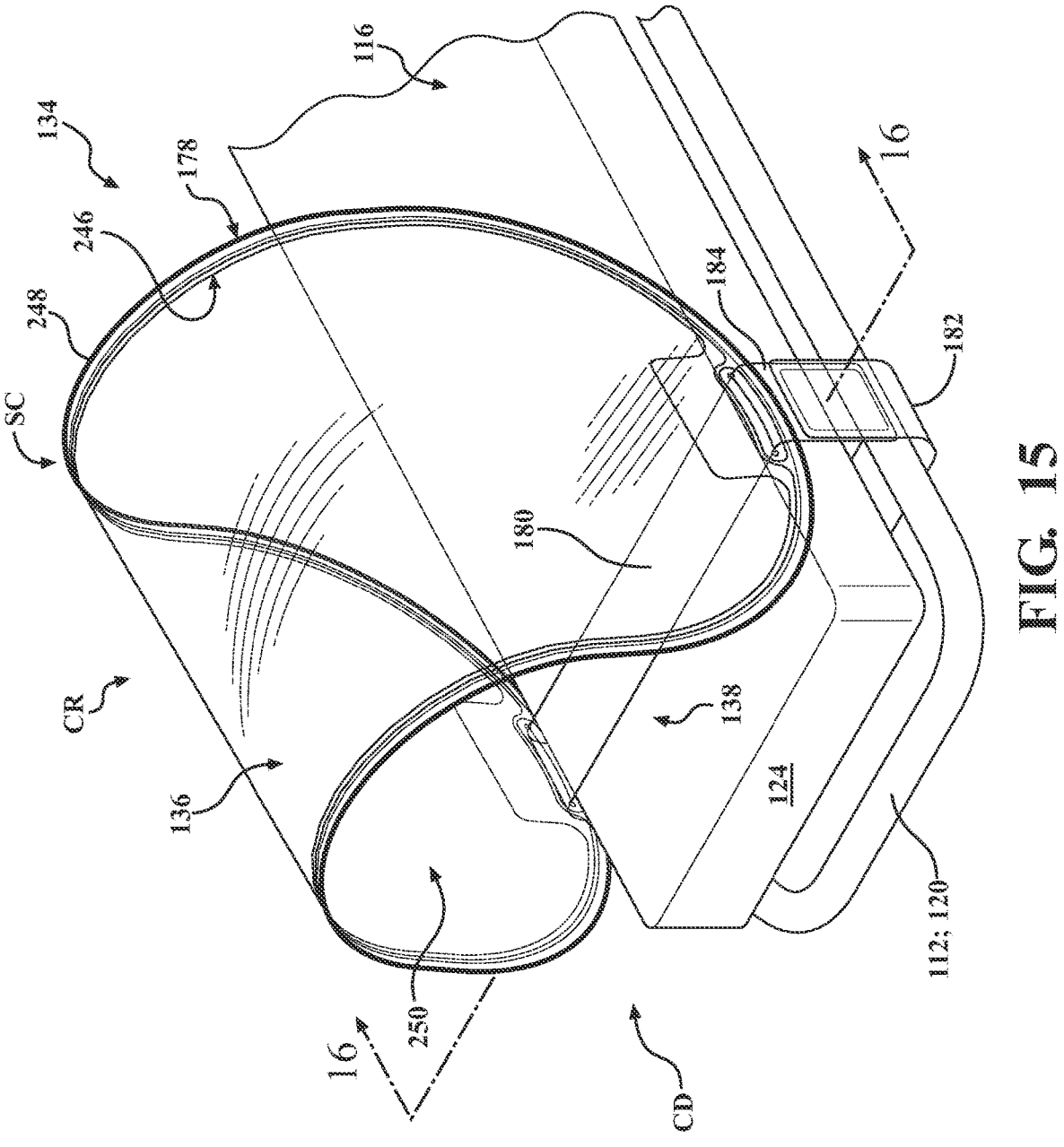
FIG. 15 is a partial perspective view of the shield assembly of FIG. 14 shown with the first retainer strap attached to the second retainer strap to secure the shield assembly to a portion of a back section and a mattress of a litter.

As noted above, the shield assembly 134 may be config-
ured such that the barrier panel 136, the first drape panel
142A, and/or the second drape panel 142B are manufactured
from a relatively transparent material. Referring now to
FIGS. 12 and 13, the illustrated embodiment of the shield
assembly 134 comprises a pouch 220 coupled to the distal
end of the barrier panel 136 (and/or to support frame 178) to
which an auxiliary drape panel 142C is stored and secured.
Similar to the first and second drape panels 142A, 142B, the
auxiliary drape panel 142C may be operatively attached to
the support frame 178 or the pouch 220 and extend away
from the closed periphery 246 to an auxiliary drape edge
166C. Here, the auxiliary drape panel 142C may be manu-
factured from a material that is more opaque, tinted, and/or
"frosted" (e.g., non-transparent) than the barrier panel 136,
and may be selectively extended out of or otherwise
removed from the pouch 220 over the barrier panel 136 or
other portions of the shield assembly 134 to define a
movable auxiliary privacy portion 254 of the shield assem-
bly 134. Said differently, the auxiliary drape panel 142C can be placed over the barrier panel 136 and/or the first and second drape panels 142A, 142B in a temporary manner to optionally afford the patient with additional privacy, shade, and the like. Thus, the auxiliary drape panel 142C may be selectively deployed and stored. The auxiliary drape panel 142C may be coupled to the pouch 220 or to another portion of the shield assembly 134, or may be removable and transferable between other shield assemblies 134. Other configurations are contemplated. In some embodiments, one or more portions of the shield assembly 134 may be manufactured from materials that provide varying opacity (e.g., transitioning between transparent and tinted), and/or which filter light in predetermined ways.

In some embodiments, the pouch 220 may be utilized to accommodate other components, such as a wrap line 222 (see FIG. 13; depicted schematically) that can be used to manage the shape and/or size of the shield assembly 134 in preparation for disposal. Here, for example, the wrap line 222 may comprise a strap, belt, and the like, which can be used to hold the shield assembly 134 in a "rolled-up" configuration to ease disposal. To this end, the shield assembly 134 may be "rolled-up" or otherwise folded in on itself so as to minimize potentially spreading particulates disposed on the inside surface during handling at disposal. Similarly, it is also contemplated that the pouch 220 could be sized, shaped, and/or located so as to facilitate storing or otherwise accommodating the shield assembly 134 at disposal (e.g., with or without the use of the wrap line 222). In some embodiments, the wrap line 222 or another portion of the shield assembly 134 could be employed as a "carry handle" to facilitate moving, deploying, stowing, or otherwise handling of the shield assembly 134. Other configurations are contemplated. In some embodiments, a filtered port (not shown) may be provided in fluid communication with the area inside of the barrier panel 136 to promote evacuation of air while the shield assembly 134 is "rolled-up" or otherwise prepared for disposal. Here, the filtered port may be configured to prevent a volume of air from being "trapped" that would otherwise increase the overall size of the shield assembly 134 for disposal. It will be appreciated that various types of filters could be utilized to limit egress of contaminants through the filtered port as air is evacuated.

In some embodiments, the shield assembly 134 could be utilized in connection with one or more types of systems, devices, or components which regulate, adjust, condition, or otherwise promote airflow movement, such as for example ventilation systems, negative pressure systems, air condition systems, oxygen supply systems, and the like. Here, it will be appreciated that these types of systems can be employed to, among other things, exchange air across the barrier such as via various arrangements of fans, pumps, filters, hoses, tubes, lines, and the like, and/or combinations thereof. Other configurations are contemplated. In some embodiments, oxygen may be supplied to the patient via a conventional nasal or face mask connected to an external oxygen source while the patient is disposed within the accommodation space 250 defined by the shield assembly 134. In some embodiments, a ventilation system could be employed to direct air out of the accommodation space 250 and away from caregivers (e.g., through a tube connected to an air pump or ventilation fan which vents in a controlled fashion and may be filtered). Other configurations are contemplated.

As noted above, the drape panels 142 may be of various sizes, types, and/or configurations. In some embodiments, the peripheral edges of the drape panels 142 and/or other portions of the shield assembly 134 may be configured to removably attach to a foundation (not shown) onto which the patient is placed. Here, for example, the peripheral edges of the drape panels 142 may be provided with a zipper that can be removably attached to a corresponding zipper formed on a rigid or semi-rigid foundation to define an isolette. In other embodiments, the peripheral edges of the drape panels 142 may be provided with zippers that can be removably attached together (and/or to other drapes) to define a body bag. It will be appreciated that the forgoing examples can be implanted in a number of different ways, using various attachment mechanisms. Other configurations are contemplated.

In some embodiments, the pouch 220 may be used to temporarily accommodate or otherwise store portions of the first drape panel 142A and/or the second drape panel 142B during handling, deployment, patient transfer, patient engagement, and the like. Similarly, clips, fasteners, and the like (not shown) may be utilized to retain one or more of the drape panels 142A, 142B temporarily. Other configurations are contemplated.

As shown in FIGS. 12-13, in some embodiments, the shield assembly 134 may be provided with a chart pouch 224 arranged for access by caregivers to store patient information in an easily-accessible location. Here, documents such as medical charts and/or patient information (and/or other documents, objects, and the like arranged for caregiver access) may be removably stored in the chart pouch 224. In some embodiments, at least a portion of the chart pouch 224 may be manufactured from a transparent material to allow the caregiver to view certain information (e.g., a medical ID number) without having to physically touch the shield assembly 134. Other configurations are contemplated.

In some embodiments, a tag 226 may be formed on or otherwise integrated with a portion of the shield assembly 134 (e.g., on the barrier panel 136). Here, the tag 226 may include a serial number or other identifying information associated with the specific shield assembly 134 to which it is attached. The tag 226 may comprise a series of alphanumeric characters (e.g., serial, batch, and/or model numbers, manufacturing dates, and the like), symbols (e.g., a bar code, a quick response QR code, and the like), and/or electronic tags (e.g., a Near Field Communication NFC tag, a Radio-Frequency Identification RFID tag, a Bluetooth tag, and the like). Here, it will be appreciated that various types of computer systems may be utilized to, among other things, read information from one or more types of tags 226, update computer databases with information associated with one or more types of tags 226, facilitate tracing of information associated with one or more types of tags 226, and the like. By way of non-limiting example, a tag 226 realized as a QR code could be scanned by a caregiver's portable electronic device to associate a specific shield assembly 134 with a specific patient. Based on this association, information about the patient (e.g., medical records indicating a positive test result for a communicable disease) can be used to facilitate contact tracing with each caregiver that treated the patient or was otherwise near the shield assembly 134 utilized by the patient. Other configurations are contemplated.

In some embodiments, the shield assembly 134 may comprise one or more manually-engageable indicators 228, which serve as Boolean indicators (e.g., a bubble or other shape that can be popped, punched out, or otherwise deformed). Here, for example, an indicator 228 can be manually engaged by a caregiver once a non-contagious patient has been cleared and the shield assembly 134 they had been utilizing has been cleaned and is ready for another patient. Thus, each indicator 228 may be used to indicate how many times a particular shield assembly 134 has been "used" by different patients. It will be appreciated that indicators 228 may be utilized for other purposes, and may be of various types, styles, and/or configurations.

In some embodiments, various types of chemical indicators may be utilized to indicate various changes in the shield assembly 134, such as to indicate when improper chemicals have been applied to the shield assembly 134, to indicate when the shield assembly 134 has been exposed to excessive heat or sunlight, and the like. In some embodiments, various types of sensors 230 may be attached to or otherwise integrated into the shield assembly 134. Here, for example, sensors 230 may be utilized to monitor utilization of the shield assembly 134 (e.g., temperature, humidity, light exposure, vibration, and the like). In addition, various types of sensors 230 may be utilized to monitor patient conditions (e.g., body temperature, perspiration, breathing patterns, heart rate, the presence of pathogens, and the like). Other configurations are contemplated.

In some embodiments, the shield assembly 134 may be provided with a flexible barrier interface 232 (e.g., coupled to or otherwise formed in the barrier panel 136) arranged for patient access adjacent to their head. Here, similar to the windows 140 described below, which may be outfitted with gloves to maintain the boundary between the patient and the caregiver, the barrier interface 232 may allow the caregiver to direct tools, instruments, and the like to the patient. For example, the caregiver may position a temperature probe into the barrier interface 232 and ask the patient to place the probe (along with the barrier interface 232) inside their mouth, ear, and the like. The barrier interface 232 may be formed integrally with the barrier panel 136 or another part of the shield assembly 134, or may be removable or replaceable. In some embodiments, the barrier interface 232 may be configured to receive a specific type of instrument, probe, and the like (e.g., as a sheath or cup for a thermometer). In some embodiments, the barrier interface 232 may house a flexible probe tip and a tether that extends to outside of the shield assembly 134 for connection to a modular thermometer. In some embodiments, the barrier interface 232 (or another portion of the shield assembly 134) may be configured to support a contactless (e.g., infrared) thermometer within a predetermined distance of the patient's skin. In some embodiments, the barrier interface 232 may include valve 234 (see FIGS. 12-13; depicted schematically), which may be used to transfer oral medication to a conscious patient. Here, the valve 234 may be configured to be one-way, may be selectively opened/closed, and the like. Other configurations are contemplated.

With continued reference to FIGS. 12 and 13, in some embodiments, the shield assembly 134 may comprise a patient pouch 236 operatively attached to the inside of the barrier panel 136 or another portion of the shield assembly 134 that the patient has access to. Here, the patient pouch 236 may be shaped and arranged to hold the patient's belongings, such as a personal electronic device 238. In some embodiments, the shield assembly 134 may comprise a user interface (not shown) arranged for access by the patient, such as a flexible display screen attached to the barrier panel 136 and arranged for viewing by the patient.

In some embodiments, one or more ports 240 may be utilized to facilitate management of lines 242, such as electrical cables (e.g., a charging cable for the patient's portable electronic device 238, leads for an Electrocardiogram ECG, leads for a pulse oximeter, and the like), air hoses (e.g., oxygen supply, ventilation, and the like), liquid tubes (e.g., intravenous lines, arterial lines, and the like), and the like between the area within the shield assembly 134 and the outside environment. Here, the ports 240 may be configured to allow lines 242 to be routed therethrough and then closed or otherwise sealed and remain in place securing around the lines 242 to minimize ingress/egress of contaminants. The ports 240 may be of a number of different sizes, styles, shapes, and/or configurations. In some embodiments, ports 240 may be realized with elastic or otherwise resilient materials that "close" slits or openings around lines 242 passed therethrough. In some embodiments, ports 240 may comprise flaps, zippers, or other barriers that permit routing of lines 242 along a tortious path. In some embodiments, ports 240 may be realized as "sealed' manifolds 244 for electrical communication, fluid (e.g., air, liquid) communication, and the like, where separate lines 242 are attached to the manifolds 244 inside and outside of the shield assembly 134. Other configurations are contemplated.

Figure 23:
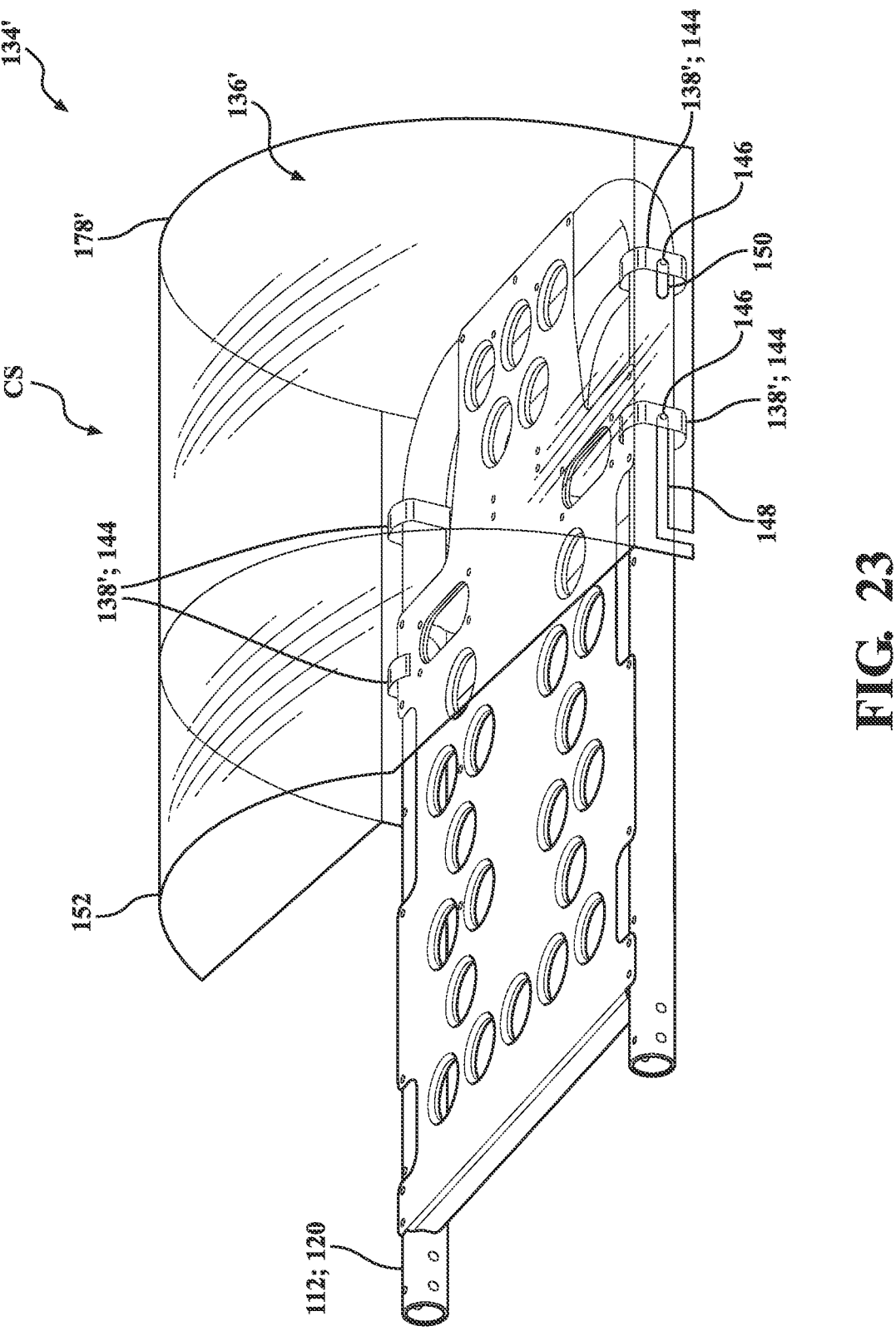
FIG. 23 is a perspective view of the back section and a shield assembly, shown with a barrier panel of the shield assembly arranged in a secured configuration.
Figure 24:
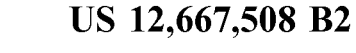
FIG. 24 is a perspective view of a back section of a litter to which a shield assembly is secured, according to embodiments of the present disclosure.

Referring now to FIGS. 23 and 24, in the illustrated embodiment, the barrier panel 136' of the shield assembly 134' is realized by a semi-rigid, flexible material, and the base 138' is realized by four clips 144, which may be removably attachable to opposing lateral sides of the back section 120 of the litter 112. For example, the barrier panel 136' may be formed from a semi-rigid, flexible material. Here, while not depicted in FIGS. 23-24, it will be appreciated that the shield assembly 134' could employ drape panels 142 formed from a thin, flexible material, as described above, that is operatively attached to the barrier panel 136' or another portion of the shield assembly 134'. In the illustrated embodiment, the clips 144 each comprise a guidepin 146 with generally cylindrical profiles extending laterally from the clips 144 (not shown in detail). The guidepins 146 are disposed within distal slots 148 and proximal slots 150 formed in the barrier panel 136' to, among other things, retain the barrier panel 136' relative to the clips 144 of the base 138' (and, thus, to the patient support apparatus 100). Here, the engagement of the guidepins 146 within the slots 148, 150 also facilitates providing the barrier panel 136' with a curved configuration CR or shape. Thus, when not attached to the clips 144 of the base 138', the illustrated embodiment of the barrier panel 136' may be substantially flat. However, the barrier panel 136' could also be pre-curved in some embodiments. In some embodiments, the barrier panel 136' is provided with an awning 152 formed, contoured, or otherwise arranged at the distal end to, among other things, extend the barrier along the patient's torso and provide room for the patient's shoulders.

In FIG. 23, the barrier panel 136' is arranged secured to the patient support apparatus 100 with two guidepins 146 of respective clips 144 of the base 138' disposed within corresponding distal slots 148, and with two guidepins 146 of respective clips 144 disposed within corresponding proximal slots 150. Here, the shield assembly 134' may be used during transport of the patient. The barrier panel 136' may be arranged in a tilted configuration (not shown) without guidepins 146 disposed within the distal slots 148. In the illustrated embodiment, the distal slots 148 have substantially L-shaped profiles that are open toward the edge of the barrier panel 136' to allow the guidepins 146 to be slid into and out of the distal slots 148 (not shown in detail), whereas the proximal slots 150 each have a substantially linear profile, which retains the respective guidepins 146 (e.g., once inserted therein; not shown in detail). It will be appreciated that the tilted configuration may be used during patient positioning onto or off of the litter 112, during patient treatment, and the like. Other configurations are contemplated.

As noted above, while the embodiment of the base 138' depicted in FIG. 23 comprises four clips 144 with respective guidepins 146, other configurations are contemplated. By way of non-limiting example, the clips 144 could be configured in a number of different ways sufficient to be removably attached to the litter 112, and may be single-use or may be reusable. In some embodiments, the guidepins 146 could be formed as a part of the litter 112, or the arrangement could be inverted where slots are formed on the litter and guidepins are formed on the barrier panel 136'. However, other types of bases 138' are contemplated by the present disclosure, and it will be appreciated that releasable attachment of the shield assemblies 134' to the patient support apparatus 100 can be effected in various ways. In some embodiments, the base 138' could be realized by a cord, string, cable, and the like, which is routed through one or more holes (e.g., in a "laced" manner) formed on lateral sides of the barrier panel 136' (not shown) and tensioned to maintain the shape of the shield assembly 134 and facilitate attachment to the patient support apparatus 100.

Referring now to FIG. 24, another embodiment of the shield assembly 134' is shown. Here, the base 138' is realized as a plate 154 that is supported on or otherwise operatively attached to the back section 120 of the litter 112. In some embodiments, the plate 154 may be disposed between the back section 120 and the mattress 124. In some embodiments, the plate 154 may be supported on the mattress 124. The plate 154 may be operatively attached to the litter 112 in a number of different ways, such as with hook-and-loop fasteners, weak adhesives, mechanical features that mate or otherwise interlock, clips, fasteners, push rivets, key-and-slot features, detent/plunger mechanisms, and the like. In some embodiments, the weight of the patient and/or the mattress 124 could promote retention of the plate 154 to the back section 120 of the litter 112. Various embodiments of the plate 154 may also be formed integrally with the back section 120. Here too, in embodiments of the base 138 that employ the plate 154, the plate 154 may be single-use, multiple-use, and the like, and may be shaped or otherwise configured for compatibility with different styles and/or types of patient support apparatuses 100 (e.g., cots from different manufacturers, stair chairs, back boards, and the like). To this end, and as is depicted in FIG. 24, the plate 154 may be shaped so as not to inhibit access to portions of the back section 120, such as apertures utilized for patient restraint strap routing (not shown in detail). Other configurations are contemplated.

In some embodiments, the base 138 may be configured to secure to, or otherwise be supported by, the patient for concurrent movement (e.g., during ambulation, ingress to and/or egress from patient support apparatuses, and the like). Thus, in addition to removably attaching to different types of patient support apparatuses 100, it will be appreciated that embodiments of the shield assembly 134, 134' of the present disclosure may also be configured to "travel" with the patient beyond moving with the patient between different patient support apparatuses 100 (e.g., similar to, or as a part of, a "gown"). Here, for example, various portions of the shield assembly 134, 134' may be manufactured from radiolucent materials, and an ambulatory patient can hold or otherwise move concurrently with the shield assembly 134, 134' to receive an x-ray without necessarily being required to fully remove the shield assembly 134, 134'. Here too, it will be appreciated that the base 138 may be configured to secure to the patient (e.g., as a belt) to facilitate concurrent movement during ambulation. Thus, besides being utilized for patients undergoing treatment or observation, embodiments of the shield assemblies 134, 134' of the present disclosure may also be utilized to promote improved safety during various types of travel, both to help prevent transmission of communicable diseases to the person protected by the shield assembly 134, 134', as well as to help prevent transmission of communicable diseases egressing from the shield assembly 134, 134'. In some embodiments, shield assemblies 134, 134' may be worn or otherwise move with a patient or person utilizing public or private transportation (e.g., in a car, airplane, train, subway, ship, and the like). In some embodiments, shield assemblies 134, 134' may be worn or otherwise move with a patient or person being detained (e.g., a combative patient, a person under arrest, and the like). Other configurations are contemplated.

In this way, the shield assemblies 134, 134' of the present disclosure afford significant advantages relating to caregiver safety and patient treatment by providing a barrier between the patient and the caregiver. Here, for example, the shield assemblies 134, 134' help to contain or otherwise prevent the dispersal of particulates, micro-contaminants, and the like, which may be expelled by the patient (e.g., out the patient's nose or mouth) and could otherwise be directed toward the caregiver, as well as helping to limit the direction of particulates, micro-contaminants, and the like which could be directed towards the patient. It will further be appreciated that the barrier afforded by the shield assemblies 134, 134' also provides the caregiver (and others nearby) with additional protection (e.g., in addition to protection from a mask, head-mounted face shield, and the like) without significantly inhibiting the ability of the caregiver to treat and transport the patient supported by the patient support apparatus 100.

It will be appreciated that the shield assemblies 134, 134' of the present disclosure can be utilized in an efficient, low-cost manner while, at the same time, allowing the caregiver to effectively treat and/or transport the patient. Specifically, it will be appreciated that the shield assemblies 134, 134' can be quickly set up and disposed of when needed, and can be utilized so as to allow the patient to be treated effectively by the caregiver while supported on the patient support apparatus 100. Moreover, in some embodiments, the shield assemblies 134, 134' described herein afford the ability to transfer the patient between different patient support apparatuses 100 such as cots, stair chairs, back boards, wheel chairs, and the like (and/or to or from patient support apparatuses such as hospital beds, stretchers, tables, and the like) without having to disassemble the shield assembly 134, 134' or detach the shield assembly 134, 134' from the patient support apparatus 100.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology that has been used is intended to be in the nature of words of description rather than of limitation. Many modifications and variations are possible in light of the above teachings and the invention may be practiced otherwise than as specifically described.

The present disclosure also comprises the following clauses, with specific features laid out in dependent clauses, that may specifically be implemented as described in greater detail with reference to the configurations and drawings above.

CLAUSES

I. A shield assembly for providing a barrier adjacent to a patient disposed on a patient support apparatus, the shield assembly comprising:
  a support frame defining a closed periphery, the support frame including a resilient element extending along the closed periphery to resiliently urge the support frame toward a bias frame shape;
  a barrier panel coupled to the support frame and spanning the closed periphery; and
  a base operatively attached to the support frame to selectively place the support frame in a contour frame shape, different from the bias frame shape, and to limit resilient movement of the support frame toward the bias frame shape;
  wherein tension in the resilient element effected by the base holding the support frame in the contour frame shape places the barrier panel in a curved configuration to define a patient accommodation space shaped to receive the patient adjacent to the base and to the barrier panel.

II. The shield assembly as set forth in clause I, wherein the support frame is selectively adjustable from the contour frame shape to a collapsed frame shape where the resilient element is twisted over itself.

III. The shield assembly as set forth in any of clauses I to II, wherein the base is operatively attached to the support frame at a first location and at a second location spaced from the first location about the closed periphery.

IV. The shield assembly as set forth in clause III, wherein the base includes a base strap extending between the first location and the second location on the support frame.

V. The shield assembly as set forth in clause IV, wherein the base strap includes a first retainer strap extending from the first location on the support frame to a first retainer strap end, and a second retainer strap extending from the second location on the support frame to a second retainer strap end; and
  wherein the first retainer strap and the second retainer strap releasably secure the shield assembly to the patient support apparatus.

VI. The shield assembly as set forth in clause V, wherein the first retainer strap includes a first fastening region disposed adjacent to the first retainer strap end, the second retainer strap includes a second fastening region disposed adjacent to the second retainer strap end, and the first fastening region is configured to releasably engage the second fastening region to secure the first retainer strap to the second retainer strap.

VII. The shield assembly as set forth in clause VI, wherein one of the first fastening region and the second fastening region comprises a hook fastening material, and the other of the first fastening region and the second fastening region comprises a loop fastening material configured to releasably engage the hook fastening material.

VIII. The shield assembly as set forth in clause VII, further comprising an extension strap including a first fastening region and a second fastening region disposed adjacent to opposing ends of the extension strap, wherein one of the first fastening region of the extension strap and the second fastening region of the extension strap comprises a hook fastening material, and the other of the first fastening region of the extension strap and the second fastening region of the extension strap comprises a loop fastening material configured to releasably engage first and second retainer straps.

IX. The shield assembly as set forth in any of clauses V to VII, wherein a first strap slot is formed in the barrier panel adjacent to the first location of the support frame, with the first retainer strap extending through the first strap slot away from the patient accommodation space; and
  wherein a second strap slot is formed in the barrier panel adjacent to the second location of the support frame, with the second retainer strap extending through the second strap slot away from the patient accommodation space.

X. The shield assembly as set forth in clause IX, wherein the barrier panel includes a first reinforced region arranged adjacent to the first location of the support frame, with the first strap slot formed in the first reinforced region; and
  wherein the barrier panel includes a second reinforced region arranged adjacent to the second location of the support frame, with the second strap slot formed in the second reinforced region.

XI. The shield assembly as set forth in any of clauses I to X, wherein the barrier panel has a substantially flat profile when the support frame is in the bias frame shape.

XII. The shield assembly as set forth in any of clauses I to XI, wherein the barrier panel has a substantially curved profile when the support frame is in the contour frame shape.

XIII. The shield assembly as set forth in any of clauses I to XII, further comprising a drape panel coupled to the support frame and extending away from the closed periphery to a drape edge to define a draped area in communication with the patient accommodation space when the support frame is disposed in the contour frame shape.

XIV. The shield assembly as set forth in clause XIII, wherein the drape panel comprises a semi-transparent material.

XV. The shield assembly as set forth in clause XIV, wherein the barrier panel comprises a transparent material.

XVI. The shield assembly as set forth in clause XV, wherein the barrier panel defines a window portion of the shield assembly; and
  wherein the drape panel defines a privacy portion of the shield assembly.

XVII. The shield assembly as set forth in any of clauses XIII to XV, further including a drape strap operatively attached to the drape panel arranged to releasably secure the drape panel to the patient support apparatus.

XVIII. The shield assembly as set forth in clause XVII, wherein the drape strap is defined by a perforated path formed in the drape panel adjacent to the drape edge.

XIX. The shield assembly as set forth in clause XVIII, wherein the drape strap includes a pull tab disposed adjacent to the perforated path and arranged for user engagement to facilitate tearing the drape strap away from the drape panel along the perforated path.

XX. The shield assembly as set forth in clause XIX, wherein the drape strap is arranged on a first lateral side of the drape panel; and further including a second drape strap arranged on a second lateral side of the drape panel.

XXI. The shield assembly as set forth in any of clauses I to XX, further comprising:

a first drape panel coupled to the support frame and extending away from the closed periphery to a first drape edge to define a first draped area in communication with the patient accommodation space when the support frame is disposed in the contour frame shape; and a second drape panel coupled to the support frame and extending away from the closed periphery to a second drape edge to define a second draped area in communication with the patient accommodation space when the support frame is disposed in the contour frame shape.

XXII. The shield assembly as set forth in clause XXI, wherein the first drape panel comprises a transparent material;

wherein the barrier panel comprises a transparent material; and wherein the second drape panel comprises a semi-transparent material.

XXIII. The shield assembly as set forth in clause XXII, wherein the barrier panel and the first drape panel cooperate to define a window portion of the shield assembly; and wherein the second drape panel defines a privacy portion of the shield assembly.

XXIV. The shield assembly as set forth in clause XXIII, further comprising an auxiliary drape panel operatively attached to the support frame, comprising a semi-transparent material, and extending away from the closed periphery to an auxiliary drape edge, the auxiliary drape panel configured to lay across at least a portion of the barrier panel to define a movable auxiliary privacy portion of the shield assembly.

XXV. The shield assembly as set forth in any of clauses XXI-XXIV, wherein the first drape panel has a larger area than the second drape panel.

XXVI. A shield assembly for providing a barrier adjacent to a patient disposed on a patient support apparatus, the shield assembly comprising:

a support frame defining a closed periphery, the support frame including a resilient element extending along the closed periphery to resiliently urge the support frame toward a bias frame shape;

a barrier panel coupled to the support frame and spanning the closed periphery;

a drape panel coupled to the support frame and extending away from the closed periphery to a drape edge; and a base operatively attached to the support frame to selectively place the support frame in a contour frame shape, different from the bias frame shape, and to limit resilient movement of the support frame toward the bias frame shape;

wherein tension in the resilient element effected by the base holding the support frame in the contour frame shape places the barrier panel in a curved configuration to define a patient accommodation space shaped to receive the patient adjacent to the base and to the barrier panel; and wherein the drape panel defines a draped area in communication with the patient accommodation space when the support frame is disposed in the contour frame shape.

XXVII. The shield assembly as set forth in clause XXVI, wherein the support frame is selectively adjustable from the contour frame shape to a collapsed frame shape where the resilient element is twisted over itself.

XXVIII. The shield assembly as set forth in any of clauses XXVI to XXVII, wherein the base is operatively attached to the support frame at a first location and at a second location spaced from the first location about the closed periphery.

XXIX. The shield assembly as set forth in clause XXVIII, wherein the base includes a base strap extending between the first location and the second location on the support frame.

XXX. The shield assembly as set forth in clause XXIX, wherein the base strap further includes a first retainer strap extending from the first location on the support frame to a first retainer strap end, and a second retainer strap extending from the second location on the support frame to a second retainer strap end; and wherein the first retainer strap and the second retainer strap releasably secure the shield assembly to the patient support apparatus.

XXXI. The shield assembly as set forth in clause XXX, wherein the first retainer strap includes a first fastening region disposed adjacent to the first retainer strap end, the second retainer strap includes a second fastening region disposed adjacent to the second retainer strap end, and the first fastening region is configured to releasably engage the second fastening region to secure the first retainer strap to the second retainer strap.

XXXII. The shield assembly as set forth in clause XXXI, wherein one of the first fastening region and the second fastening region comprises a hook fastening material, and the other of the first fastening region and the second fastening region comprises a loop fastening material configured to releasably engage the hook fastening material.

XXXIII. The shield assembly as set forth in clause XXXII, further comprising an extension strap including a first fastening region and a second fastening region disposed adjacent to opposing ends of the extension strap, wherein one of the first fastening region of the extension strap and the second fastening region of the extension strap comprises a hook fastening material, and the other of the first fastening region of the extension strap and the second fastening region of the extension strap comprises a loop fastening material configured to releasably engage first and second retainer straps.

XXXIV. The shield assembly as set forth in any of clauses XXX to XXXIII, wherein a first strap slot is formed in the barrier panel adjacent to the first location of the support frame, with the first retainer strap extending through the first strap slot away from the patient accommodation space; and wherein a second strap slot is formed in the barrier panel adjacent to the second location of the support frame, with the second retainer strap extending through the second strap slot away from the patient accommodation space.

XXXV. The shield assembly as set forth in clause XXXIV, wherein the barrier panel includes a first reinforced region arranged adjacent to the first location of the support frame, with the first strap slot formed in the first reinforced region; and wherein the barrier panel includes a second reinforced region arranged adjacent to the second location of the support frame, with the second strap slot formed in the second reinforced region.

XXXVI. The shield assembly as set forth in any of clauses XXVI to XXXV, wherein the barrier panel has a substantially flat profile when the support frame is in the bias frame shape.

XXXVII. The shield assembly as set forth in any of clauses XXVI to XXXVI, wherein the barrier panel has a substantially curved profile when the support frame is in the contour frame shape.

XXXVIII. The shield assembly as set forth in any of clauses XXVI to XXXVII, wherein the drape panel has a substantially flat profile when the support frame is in the bias frame shape.

XXXIX. The shield assembly as set forth in any of clauses XXVI to XXXVIII, wherein the drape panel comprises a semi-transparent material.

XL. The shield assembly as set forth in clause XXXIX, wherein the barrier panel comprises a transparent material.

XLI. The shield assembly as set forth in clause XL, wherein the barrier panel defines a window portion of the shield assembly; and wherein the drape panel defines a privacy portion of the shield assembly.

XLII. The shield assembly as set forth in any of clauses XXVI to XLI, further including a drape strap operatively attached to the drape panel arranged to releasably secure the drape panel to the patient support apparatus.

XLIII. The shield assembly as set forth in clause XLII, wherein the drape strap is defined by a perforated path formed in the drape panel adjacent to the drape edge.

XLIV. The shield assembly as set forth in clause XLIII, wherein the drape strap includes a pull tab disposed adjacent to the perforated path and arranged for user engagement to facilitate tearing the drape strap away from the drape panel along the perforated path.

XLV. The shield assembly as set forth in clause XLIV, wherein the drape strap is arranged on a first lateral side of the drape panel; and further including a second drape strap arranged on a second lateral side of the drape panel.

XLVI. The shield assembly as set forth in any of clauses XXVI to XLV, wherein the drape panel is further defined as a first drape panel coupled to the support frame and extending away from the closed periphery to a first drape edge to define a first draped area in communication with the patient accommodation space when the support frame is disposed in the contour frame shape; and further comprising a second drape panel coupled to the support frame and extending away from the closed periphery to a second drape edge to define a second draped area in communication with the patient accommodation space when the support frame is disposed in the contour frame shape.

XLVII. The shield assembly as set forth in clause XLVI, wherein the first drape panel comprises a transparent material;

wherein the barrier panel comprises a transparent material; and wherein the second drape panel comprises a semi-transparent material.

XLVIII. The shield assembly as set forth in clause XLVII, wherein the barrier panel and the first drape panel cooperate to define a window portion of the shield assembly; and wherein the second drape panel defines a privacy portion of the shield assembly.

XLIX. The shield assembly as set forth in clause XLVIII, further comprising an auxiliary drape panel operatively attached to the support frame, comprising a semi-transparent material, and extending away from the closed periphery to an auxiliary drape edge, the auxiliary drape panel configured to lay across at least a portion of the barrier panel to define a movable auxiliary privacy portion of the shield assembly.

L. The shield assembly as set forth in any of clauses XLVI to XLIX, wherein the first drape panel has a larger area than the second drape panel.

What is claimed is:

1. A shield assembly for providing a barrier adjacent to a patient disposed on a patient support apparatus, the shield assembly comprising:

a support frame defining a closed periphery, the support frame including a resilient element extending along the closed periphery to resiliently urge the support frame toward a bias frame shape;

a barrier panel coupled to the support frame and spanning the closed periphery;

a drape panel coupled to the support frame and extending away from the closed periphery to a drape edge;

a drape strap operatively attached to the drape panel arranged to releasably secure the drape panel to the patient support apparatus, wherein the drape strap is defined by a perforated path formed in the drape panel adjacent to the drape edge; and a base operatively attached to the support frame to selectively place the support frame in a contour frame shape, different from the bias frame shape, and to limit resilient movement of the support frame toward the bias frame shape;

wherein tension in the resilient element effected by the base holding the support frame in the contour frame shape places the barrier panel in a curved configuration to define a patient accommodation space shaped to receive the patient adjacent to the base and to the barrier panel; and wherein the drape panel defines a draped area in communication with the patient accommodation space when the support frame is disposed in the contour frame shape.

2. The shield assembly as set forth in claim 1, wherein the support frame is selectively adjustable from the contour frame shape to a collapsed frame shape where the resilient element is twisted over itself.

3. The shield assembly as set forth in claim 1, wherein the base is operatively attached to the support frame at a first location and at a second location spaced from the first location about the closed periphery.

4. The shield assembly as set forth in claim 3, wherein the base includes a base strap extending between the first location and the second location on the support frame.

5. The shield assembly as set forth in claim 4, wherein the base strap further includes a first retainer strap extending from the first location on the support frame to a first retainer strap end, and a second retainer strap extending from the second location on the support frame to a second retainer strap end; and wherein the first retainer strap and the second retainer strap releasably secure the shield assembly to the patient support apparatus.

6. The shield assembly as set forth in claim 5, wherein the first retainer strap includes a first fastening region disposed adjacent to the first retainer strap end, the second retainer strap includes a second fastening region disposed adjacent to the second retainer strap end, and the first fastening region is configured to releasably engage the second fastening region to secure the first retainer strap to the second retainer strap;

wherein one of the first fastening region and the second fastening region comprises a hook fastening material, and the other of the first fastening region and the second fastening region comprises a loop fastening material configured to releasably engage the hook fastening material; and further comprising an extension strap including a first fastening region and a second fastening region disposed adjacent to opposing ends of the extension strap, wherein one of the first fastening region of the extension strap and the second fastening region of the extension strap comprises a hook fastening material, and the other of the first fastening region of the extension strap and the second fastening region of the extension strap comprises a loop fastening material configured to releasably engage first and second retainer straps.

7. The shield assembly as set forth in claim 5, wherein a first strap slot is formed in the barrier panel adjacent to the first location of the support frame, with the first retainer strap extending through the first strap slot away from the patient accommodation space; and wherein a second strap slot is formed in the barrier panel adjacent to the second location of the support frame, with the second retainer strap extending through the second strap slot away from the patient accommodation space;

wherein the barrier panel includes a first reinforced region arranged adjacent to the first location of the support frame, with the first strap slot formed in the first reinforced region; and wherein the barrier panel includes a second reinforced region arranged adjacent to the second location of the support frame, with the second strap slot formed in the second reinforced region.

8. The shield assembly as set forth in claim 1, wherein barrier panel has a substantially flat profile when the support frame is in the bias frame shape; and wherein the barrier panel has a substantially curved profile when the support frame is in the contour frame shape.

9. The shield assembly as set forth in claim 1, wherein the drape panel has a substantially flat profile when the support frame is in the bias frame shape.

10. The shield assembly as set forth in claim 1, wherein the drape panel comprises a semi-transparent material.

11. The shield assembly as set forth in claim 10, wherein the barrier panel comprises a transparent material;

wherein the barrier panel defines a window portion of the shield assembly; and wherein the drape panel defines a privacy portion of the shield assembly.

12. The shield assembly as set forth in claim 1, wherein the drape strap includes a pull tab disposed adjacent to the perforated path and arranged for user engagement to facilitate tearing the drape strap away from the drape panel along the perforated path.

13. The shield assembly as set forth in claim 12, wherein the drape strap is arranged on a first lateral side of the drape panel; and further including a second drape strap arranged on a second lateral side of the drape panel.

14. The shield assembly as set forth in claim 1, wherein the drape panel is further defined as a first drape panel coupled to the support frame and extending away from the closed periphery to a first drape edge to define a first draped area in communication with the patient accommodation space when the support frame is disposed in the contour frame shape; and further comprising a second drape panel coupled to the support frame and extending away from the closed periphery to a second drape edge to define a second draped area in communication with the patient accommodation space when the support frame is disposed in the contour frame shape.

15. The shield assembly as set forth in claim 14, wherein the first drape panel comprises a transparent material;

wherein the barrier panel comprises a transparent material; and wherein the second drape panel comprises a semi-transparent material.

16. The shield assembly as set forth in claim 15, wherein the barrier panel and the first drape panel cooperate to define a window portion of the shield assembly; and wherein the second drape panel defines a privacy portion of the shield assembly.

17. The shield assembly as set forth in claim 16, further comprising an auxiliary drape panel operatively attached to the support frame, comprising a semi-transparent material, and extending away from the closed periphery to an auxiliary drape edge, the auxiliary drape panel configured to lay across at least a portion of the barrier panel to define a movable auxiliary privacy portion of the shield assembly.

18. The shield assembly as set forth in claim 14, wherein the first drape panel has a larger area than the second drape panel.

19. A shield assembly for providing a barrier adjacent to a patient disposed on a patient support apparatus, the shield assembly comprising:

a support frame defining a closed periphery, the support frame including a resilient element extending along the closed periphery to resiliently urge the support frame toward a bias frame shape;

a barrier panel coupled to the support frame and spanning the closed periphery;

a drape panel coupled to the support frame and extending away from the closed periphery to a drape edge; and a base operatively attached to the support frame to selectively place the support frame in a contour frame shape, different from the bias frame shape, and to limit resilient movement of the support frame toward the bias frame shape, wherein the base is operatively attached to the support frame at a first location and at a second location spaced from the first location about the closed periphery, the base having a base strap extending between the first location and the second location on the support frame and including:

a first retainer strap extending from the first location on the support frame to a first retainer strap end, and

US 12,667,508 B2

29 a second retainer strap extending from the second
location on the support frame to a second retainer
strap end; and
wherein the first retainer strap and the second retainer
strap releasably secure the shield assembly to the 5
patient support apparatus;
wherein tension in the resilient element effected by the
base holding the support frame in the contour frame
shape places the barrier panel in a curved configuration
to define a patient accommodation space shaped to 10
receive the patient adjacent to the base and to the
barrier panel; and
wherein the drape panel defines a draped area in commu-
nication with the patient accommodation space when
the support frame is disposed in the contour frame 15
shape.

*     *     *     *     *

30